United States Patent
Liu et al.

(10) Patent No.: US 8,575,114 B2
(45) Date of Patent: Nov. 5, 2013

(54) SGLT-2 INHIBITORS, METHODS OF MAKING THEM, AND USES THEREOF

(75) Inventors: Shuang Liu, Schenectady, NY (US); Cheng Guo, Schenectady, NY (US)

(73) Assignee: Albany Molecular Research, Inc., Albany, NY (US)

( * ) Notice: Subject to any disclaimer, the term of this patent is extended or adjusted under 35 U.S.C. 154(b) by 0 days.

(21) Appl. No.: 13/052,171

(22) Filed: Mar. 21, 2011

(65) Prior Publication Data
US 2011/0237527 A1    Sep. 29, 2011

Related U.S. Application Data

(60) Provisional application No. 61/316,540, filed on Mar. 23, 2010.

(51) Int. Cl.
- *A01N 43/04* (2006.01)
- *A61K 31/70* (2006.01)
- *C07H 5/04* (2006.01)
- *C07H 5/06* (2006.01)

(52) U.S. Cl.
USPC .................................. 514/23; 536/53; 536/55

(58) Field of Classification Search
None
See application file for complete search history.

(56) References Cited

FOREIGN PATENT DOCUMENTS

| | | |
|---|---|---|
| EP | 1 577 317 A1 | 9/2005 |
| EP | 1 980 560 A2 | 10/2008 |
| WO | 2007136116 A2 | 11/2007 |
| WO | 2008013321 A1 | 1/2008 |
| WO | 2008101939 A1 | 8/2008 |

OTHER PUBLICATIONS

Wolff, Manfred E. "Burger's Medicinal Chemistry, 5ed, Part I", John Wiley & Sons, 1995, pp. 975-977.*
Banker, G.S. et al, "Modern Pharmaceutics, 3ed.", Marcel Dekker, New York, 1996, p. 596.*

* cited by examiner

*Primary Examiner* — Traviss C McIntosh, III
(74) *Attorney, Agent, or Firm* — LeClairRyan, a Professional Corporation

(57) ABSTRACT

The present invention relates to compounds which are inhibitors of sodium dependent glucose co-transporter-2 (SGLT-2). These compounds are used in the treatment of various disorders, including diabetes, impaired glucose tolerance, insulin resistance, retinopathy, nephropathy, neuropathy, cataracts, hyperglycemia, hyperinsulinemia, hyperchlolesterolemia, elevated blood level of free fatty acids or glycerol, hyperlipidemia, hypertriglyceridemia, obesity, wound healing, tissue ischemia, atherosclerosis, and hypertension. These compounds and compositions are also useful for treating and preventing kidney stones, hyperuricemia, gout, and hyponatremia. Methods of making these compounds are also described in the present invention.

7 Claims, No Drawings

SGLT-2 INHIBITORS, METHODS OF MAKING THEM, AND USES THEREOF

This application claims the benefit of U.S. Provisional Patent Application Ser. No. 61/316,540, filed Mar. 23, 2010, which is hereby incorporated by reference in its entirety.

FIELD OF THE INVENTION

The present invention relates to compounds which are inhibitors of sodium dependent glucose co-transporter-2 (SGLT-2), methods of making them, and uses thereof.

BACKGROUND OF THE INVENTION

According to the World Health Organization (WHO), in 2009, more than 220 million people worldwide have diabetes. In 2005, an estimated at least 1.1 million people died from diabetes. The WHO projects that diabetes deaths will double between 2005 and 2030.

Diabetes is a chronic disease that occurs either when the beta-cells in pancreas do not produce enough insulin or when the body cannot effectively use the insulin it produces. Insulin is a hormone that regulates blood sugar. Hyperglycaemia, or raised blood sugar, is a common effect of uncontrolled diabetes and over time leads to serious damage to many of the body's systems, especially the nerves and blood vessels. Type II diabetes (formerly called non-insulin-dependent or adult-onset) results from the body's ineffective use of insulin. Type II diabetes comprises 90% of people with diabetes around the world, and is often the result of excess body weight and physical inactivity. Effective control of blood glucose levels in diabetes patients will prevent or delay the development of diabetes complications such as cardiovascular diseases, stroke, nephropathy, retinopathy, renal failure, amputation of the extremities, and beta cell failure.

Glucose molecules pass from the bloodstream into glomerulus in the kidney, but the glucose is subsequently reabsorbed via active transport mechanisms in the proximal convoluted tubule back to the blood circulation rather than being lost with the urine. Two sodium-dependent glucose co-transporters have been identified that cause the glucose to be reabsorbed: SGLT-1 and SGLT-2. SGLT-2, which is found only in the earlier section (S1 segment) of the proximal convoluted tubule of the glomerulus, accounts for approximately 90% of the reabsorption of glucose. The other, SGLT-1, which exists in the later section (S3 segment) of the proximal tubule and is also found in the gut and other tissues, accounts for only about 10% of glucose reabsorption. In people with normal blood glucose levels, glucose is not excreted into the urine, due to the function of SGLTs.

Selective inhibitors of SGLT-2 have been demonstrated in both preclinical animal models and human clinical trials to effectively control glucose levels in the blood as well as lowering HbA1C (Han et al., *Diabetes*, 57(6):1723 (2008); List et al., *Diabetes Care*, 32(4):650 (2009); Komoroski et al., *Clin. Pharmacol. Ther.*, 85(5):520 (2009); Komoroski et al., *Clin. Pharmacol. Ther.*, 85(5):513 (2009)). In these studies, body weight reduction was often observed, indicating that SGLT-2 inhibitors could lower body weight. Humans with a mutation of the SGLT-2 gene have familial forms of renal glucosuria, providing further evidence of the primary role of SGLT-2 in renal glucose re-absorption. These patients have otherwise normal renal functions and generally have no other clinical abnormalities.

In recent years, reducing HbA1C values to <7% has become the recommended standard for patients with type II diabetes. Although there are a variety of medical therapies for type II diabetes, many patients still cannot achieve the target HbA1C level. Since all of these oral agents, except for α-glucosidase inhibitors, directly or indirectly depend on insulin to regulate blood glucose levels, type II diabetes patients eventually will rely on insulin therapy because of an inevitable decline of beta-cell function. In addition, the existing agents do not promote weight loss and some even cause weight gain. Clearly, there is an imperative demand for novel agents for the effective treatment of type II diabetes which are independent of insulin.

The present invention is directed to overcoming these and other deficiencies in the art.

SUMMARY OF THE INVENTION

One aspect of the present invention relates to a compound of formula (I):

wherein
A is O or S;
$R^1$ is H;
$R^2$ is H, halogen, CN, $OR^a$, $NR^bR^c$, $COR^d$, $CONR^bR^c$, $SO_2R^d$, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^3$ is H, halogen, methyl, ethyl, isopropyl, $CH_2OH$, $CH_2CH_2OH$, $CF_3$, or $CF_2H$;
$R^4$ is H;
$R^5$ is Cl, F, or methyl;
$R^6$, $R^7$, and $R^8$ are H;
$R^9$ is $CH_2OH$ or SMe;
$R^a$ is H, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^b$ and $R^c$ are, independently, H, $COR^d$, $SO_2R^d$, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^b$ and $R^c$ can be taken together with the nitrogen to which they are attached to form a ring which is selected from the group consisting of:

wherein each of these rings is optionally substituted 1-3 times by $R^f$ and one or two of the ring $CH_2$ units or the sulphur can be optionally substituted by an oxo or thio group;

$R^d$ is $NR^bR^c$, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;

$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^gCOR^h$, or $SO_2R^g$;

$R^f$ is halogen, $CF_3$, $CF_2H$, $OCF_3$, $OCF_2H$, CN, $OR^g$, $NR^gR^h$, $COR^g$, $CONR^gR^h$, $NCOR^gR^h$, $SO_2R^g$, lower alkyl, lower alkenyl, or lower alkynyl, wherein each lower alkyl, lower alkenyl, and lower alkynyl is optionally substituted 1-3 times by $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, or $CO_2R^g$; and $R^g$ and $R^h$ are each, independently, H, lower alkyl, lower alkenyl, or lower alkynyl;

or an oxide thereof, a pharmaceutically acceptable salt thereof, a solvate thereof, or prodrug thereof.

Another aspect of the present invention relates to a compound of formula (II):

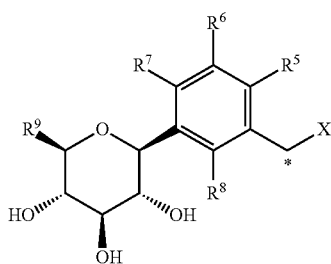

wherein X is selected from the group consisting of

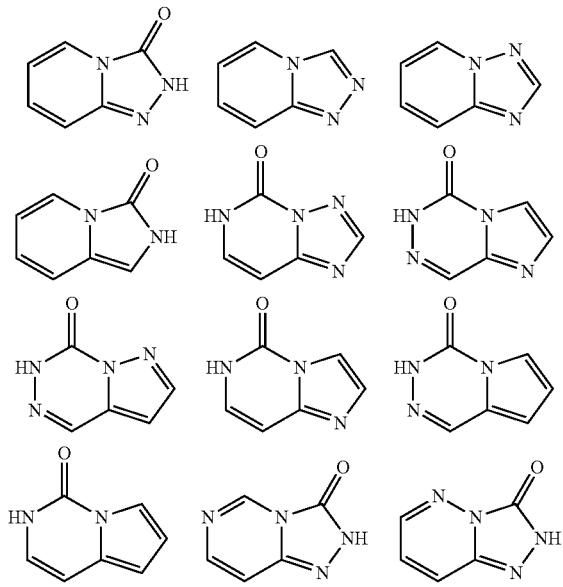

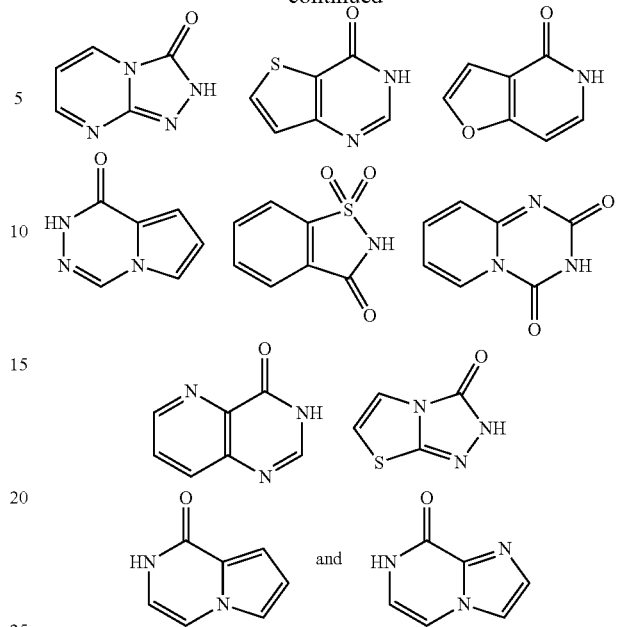

wherein each X is optionally substituted 1-3 times by $R^f$ and a $CH_2$ unit in a ring of X can be optionally substituted by oxo or thio;

$R^5$ is Cl, methyl, or F;

$R^6$ to $R^8$ are H;

$R^g$ is $CH_2OH$ or SMe;

$R^f$ is halogen, $CF_3$, $CF_2H$, $OCF_3$, $OCF_2H$, CN, $OR^g$, $NR^gR^h$, $COR^g$, $CONR^gR^h$, $NCOR^gR^h$, $SO_2R^g$, lower alkyl, lower alkenyl, or lower alkynyl, wherein each lower alkyl, lower alkenyl, and lower alkynyl is optionally substituted 1-3 times by $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, or $CO_2R^g$; and $R^g$ and $R^h$ are each, independently, H, lower alkyl, lower alkenyl, or lower alkynyl;

or an oxide thereof, a pharmaceutically acceptable salt thereof, a solvate thereof, or prodrug thereof.

An additional aspect of the present invention relates to a compound of formula (III):

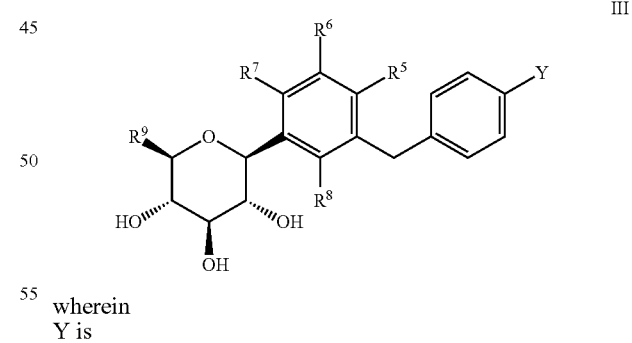

wherein
Y is

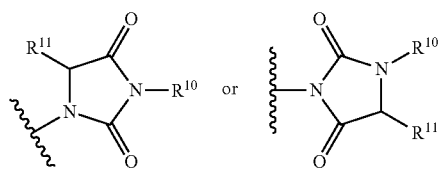

$R^5$ is Cl, F, or methyl;
$R^6$, $R^7$, and $R^8$ are H;
$R^9$ is $CH_2OH$ or SMe;

$R^{10}$ is H, lower alkyl, lower alkenyl, or lower alkynyl, wherein each lower alkyl, lower alkenyl, or lower alkynyl is optionally substituted 1-3 times by $R^e$;

$R^{11}$ is H, methyl, ethyl, or gem-dimethyl;

$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^gCOR^h$, or $SO_2R^g$; and $R^g$ and $R^h$ are each, independently, H, lower alkyl, lower alkenyl, or lower alkynyl;

or an oxide thereof, a pharmaceutically acceptable salt thereof, a solvate thereof, or prodrug thereof.

Another aspect of the present invention relates to the compound of formula (III):

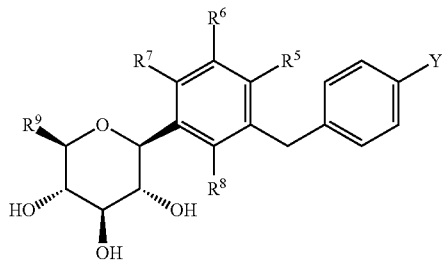

III wherein
Y is

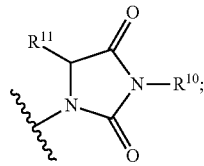

$R^5$ is Cl or methyl;
$R^6$, $R^7$ and $R^8$ are H;
$R^9$ is $CH_2OH$;
$R^{10}$ is H, lower alkyl, lower alkenyl, or lower alkynyl, wherein each lower alkyl, lower alkenyl, or lower alkynyl is optionally substituted 1-3 times by $R^e$;
$R^{11}$ is H, methyl, ethyl, or gem-dimethyl;
$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^gCOR^h$, or $SO_2R^g$; and
$R^g$ and $R^h$ are each, independently, H, lower alkyl, lower alkenyl, or lower alkynyl;
or an oxide thereof, a pharmaceutically acceptable salt thereof, a solvate thereof, or prodrug thereof.

The present invention also relates to methods of making the compounds of formulae (I), (II), and (III).

The compounds of the present invention possess inhibitory activity against sodium dependent glucose transporters, in particular, SGLT-2, found in the kidney of mammals. Thus, the compounds of the present invention are useful in the treatment of a disease or condition which is susceptible to treatment with a SGLT inhibitor. In particular, the compounds of the present invention are useful in the treatment of diabetes and micro- and macrovascular complications of diabetes such as retinopathy, neuropathy, nephropathy, and wound healing. In people with diabetes and elevated blood glucose levels, blocking the SGLT transporters can prevent the filtered glucose from returning to the blood, therefore lowering the blood glucose levels. As a result, the unabsorbed glucose can be excreted in the urine. Scientific evidence indicates that blocking SGLT-1 inhibitor could cause unwanted even fatal GI side effect (Turk et al., Nature 350:354 (1991), which is hereby incorporated by reference in its entirety), therefore selective SGLT-2 inhibitors are desirable as treatment for diabetes. In summary, selective inhibition of SGLT-2 in diabetic patients normalizes plasma glucose by increasing the excretion of glucose in the urine, therefore improving insulin sensitivity and preventing or delaying the development of diabetic complications. The function of SGLT-2 inhibitors is independent of insulin levels which makes SGLT-2 inhibitors useful at any stage of the diabetic disease and for both type I and type II diabetes. If such an agent can also lower body weight, it would provide an additional benefit to the treatment of type II diabetes since a majority of the diabetic population is also overweight.

Thus, the compounds of the present invention and/or a pharmaceutical composition employing these compounds are useful in the treatment of diabetes, such as type I and type II diabetes. These compounds and compositions are also useful in treating complications of diabetes, including retinopathy, neuropathy, nephropathy, and delayed wound healing, and related diseases such as insulin resistance (impaired glucose homeostasis), hyperglycemia, hyperinsulinemia, elevated blood levels of fatty acids or glycerol, obesity, hyperlipidemia including hypertriglyceridemia, Syndrome X, atherosclerosis, and hypertension, and for increasing high density lipoprotein levels. These compounds and compositions are also useful for treating and preventing kidney stones, hyperuricemia, and gout. These compounds and compositions are also useful for treating hyponatremia.

Further, the SGLT inhibitors of the present invention can potentially be used to in combination with other therapeutic agents. A potential significant advantage of SGLT-2 inhibitors is that they could produce weight loss due to the mechanism of actions.

DETAILED DESCRIPTION OF THE INVENTION

One aspect of the present invention relates to a compound of formula (I):

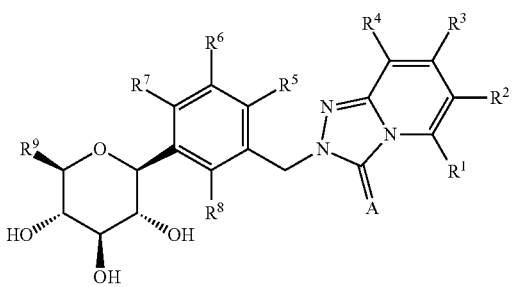

I wherein
A is O or S;
$R^1$ is H;
$R^2$ is H, halogen, CN, $OR^a$, $NR^bR^c$, $COR^d$, $CONR^bR^c$, $SO_2R^d$, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^3$ is H, halogen, methyl, ethyl, isopropyl, $CH_2OH$, $CH_2CH_2OH$, $CF_3$ or $CF_2H$;
$R^4$ is H;
$R^5$ is Cl, F or methyl;
$R^6$, $R^7$, and $R^8$ are H;
$R^9$ is $CH_2OH$ or SMe;
$R^a$ is H, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^b$ and $R^c$ are, independently, H, $COR^d$, $SO_2R^d$, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^b$ and $R^c$ can be taken together with the nitrogen to which they are attached to form a ring which is selected from the group consisting of:

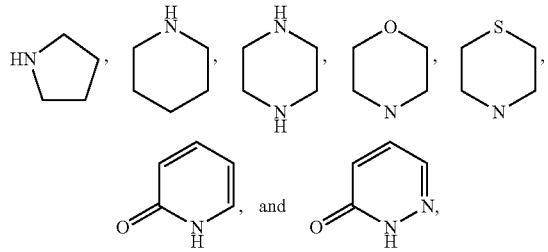

wherein each of these rings is optionally substituted 1-3 times by R' and one or two of the ring $CH_2$ units or the sulphur can be optionally substituted by an oxo or thio group;
$R^d$ is $NR^bR^c$, lower alkyl, lower alkenyl, lower alkynyl, 3 to 10-membered carbocycle, or 3 to 10-membered heterocycle, wherein each of lower alkyl, lower alkenyl, and lower alkynyl is optionally substituted from 1-3 times by $R^e$ and each 3 to 10-membered carbocycle or 3 to 10-membered heterocycle is optionally substituted 1-3 times by $R^f$;
$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^gCOR^{11}$, or $SO_2R^g$;
$R^f$ is halogen, $CF_3$, $CF_2H$, $OCF_3$, $OCF_2H$, CN, $OR^g$, $NR^gR^h$, $COR^g$, $CONR^gR^h$, $NCOR^gR^h$, $SO_2R^g$, lower alkyl, lower alkenyl, or lower alkynyl, wherein each lower alkyl, lower alkenyl, and lower alkynyl is optionally substituted 1-3 times by $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, or $CO_2R^9$; and
$R^g$ and $R^h$ are each, independently, H, lower alkyl, lower alkenyl, or lower alkynyl;
or an oxide thereof, a pharmaceutically acceptable salt thereof, a solvate thereof, or prodrug thereof.

An embodiment of the present invention relates to the compound of formula (I) wherein $R^9$ is $CH_2OH$.

Another aspect of the present invention relates to a compound of formula (II):

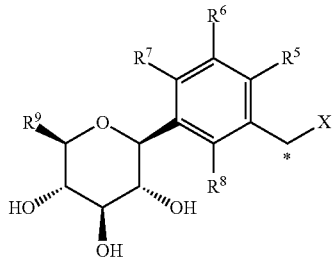

wherein X is selected from the group consisting of

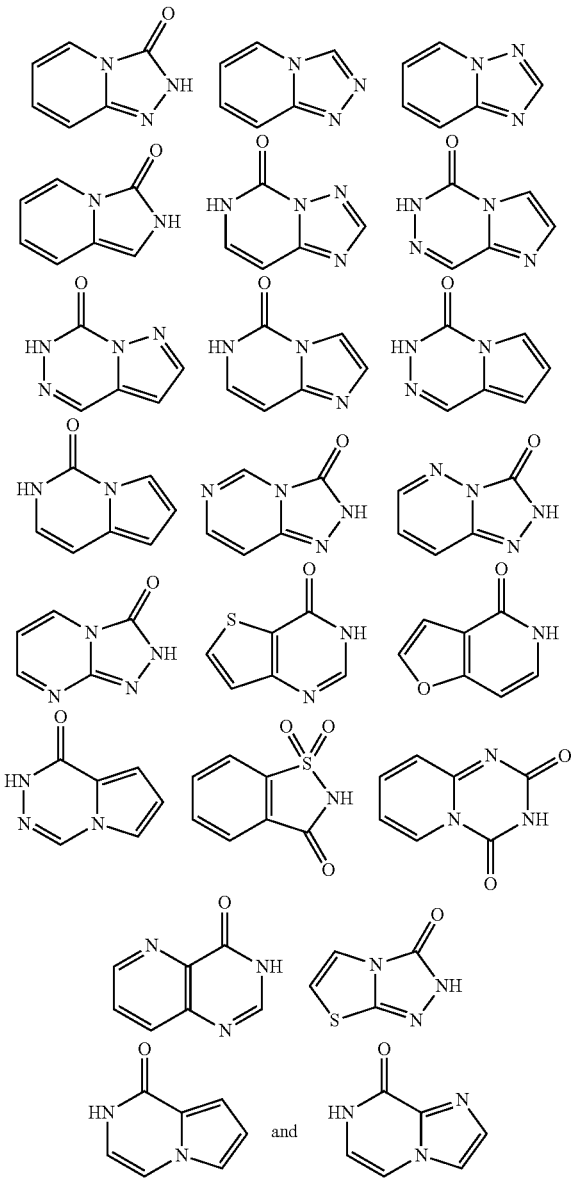

wherein each X is optionally substituted 1-3 times by $R^f$ and a $CH_2$ unit in a ring of X can be optionally substituted by oxo or thio;

$R^5$ is Cl, methyl or F;

$R^6$ to $R^8$ are H;

$R^9$ is $CH_2OH$ or SMe;

$R^f$ is halogen, $CF_3$, $CF_2H$, $OCF_3$, $OCF_2H$, CN, $OR^g$, $NR^gR^h$, $COR^g$, $CONR^gR^h$, $NCOR^gR^h$, $SO_2R^g$, lower alkyl, lower alkenyl, or lower alkynyl, wherein each lower alkyl, lower alkenyl, and lower alkynyl is optionally substituted 1-3 times by $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, or $CO_2R^9$; and $R^g$ and $R^h$ are each, independently, H, lower alkyl, lower alkenyl, or lower alkynyl;

or an oxide thereof, a pharmaceutically acceptable salt thereof, a solvate thereof, or prodrug thereof.

An embodiment of the present invention relates to the compound of formula (II) wherein $R^9$ is $CH_2OH$.

An additional aspect of the present invention relates to a compound of formula (III):

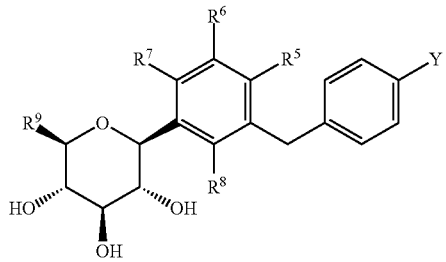

III wherein
Y is

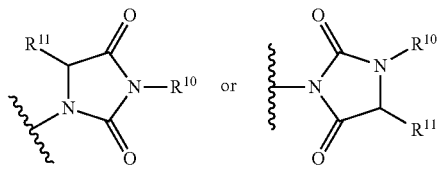

$R^5$ is Cl, F or methyl;

$R^6$, $R^7$, and $R^8$ are H;

$R^9$ is $CH_2OH$ or SMe;

$R^{10}$ is H, lower alkyl, lower alkenyl, or lower alkynyl, wherein each lower alkyl, lower alkenyl, or lower alkynyl is optionally substituted 1-3 times by $R^e$;

$R^{11}$ is H, methyl, ethyl, or gem-dimethyl;

$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^gCOR^h$, or $SO_2R^g$; and $R^g$ and $R^h$ are each, independently, H, lower alkyl, lower alkenyl, or lower alkynyl;

or an oxide thereof, a pharmaceutically acceptable salt thereof, a solvate thereof, or prodrug thereof.

Another aspect of the present invention relates to the compound of formula (III):

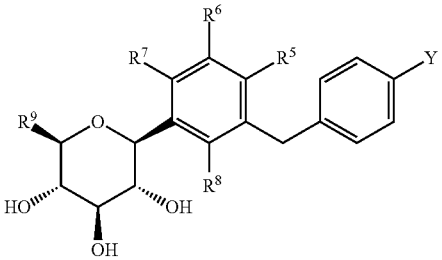

III wherein
Y is

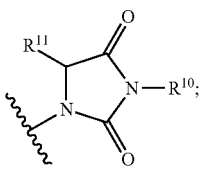

$R^5$ is Cl or methyl;

$R^6$, $R^7$, and $R^8$ are H;

$R^9$ is $CH_2OH$;

$R^{10}$ is H, lower alkyl, lower alkenyl, or lower alkynyl, wherein each lower alkyl, lower alkenyl, or lower alkynyl is optionally substituted 1-3 times by $R^e$;

$R^{11}$ is H, methyl, ethyl, or gem-dimethyl;

$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^gCOR^h$, or $SO_2R^g$; and $R^g$ and $R^h$ are each, independently, H, lower alkyl, lower alkenyl, or lower alkynyl;

or an oxide thereof, a pharmaceutically acceptable salt thereof, a solvate thereof, or prodrug thereof.

As used above, and throughout the description of the invention, the following terms, unless otherwise indicated, shall be understood to have the following meanings:

The term "lower alkyl" means an aliphatic hydrocarbon group which may be straight or branched having about 1 to about 10 carbon atoms in the chain, or a non-aromatic cyclic alkyl group with 3-10 carbons. A non-cyclic alkyl can be straight chain such as methyl, ethyl, n-propyl, n-butyl, n-pentyl, and n-hexane, or branched chain such as isopropyl, sec-butyl, and t-butyl. Representative examples of cyclic alkyls include, but are not limited to, cyclopropyl, cyclobutyl, cyclopentyl, cylcohexyl, and cycloheptyl. "Lower alkyl" in this invention also includes cyclic alkyls with alkyl substitutions, such as cyclopropylmethyl, cyclopentylmethyl, gem-dimethylcyclobutyl, and gem-dimethylcyclohexyl. The total number of carbon atoms for such a group does not exceed 10. As used herein, Me and Et mean methyl and ethyl, respectively.

The term "halo" or "halogen" means fluoro, chloro, bromo, or iodo.

When an alkyl is substituted from 1 to 3 times with halogen, the substituted groups include, for example, $CF_3$, $CF_2H$, $CH_2CF_3$, and $CH_2CF_2H$.

The term "gem-dimethyl" means two methyl groups that substitute the two hydrogen atoms on a methylene group.

The term lower "lower alkenyl" means an aliphatic hydrocarbon group containing one or more carbon-carbon double bonds and which may be straight or branched having 2 to about 10 carbon atoms in the chain. In one embodiment, the alkenyl groups have 2 to about 4 carbon atoms in the chain. Branched means that one or more lower alkyl groups such as methyl, ethyl, or propyl are attached to a linear alkenyl chain. Representative alkenyl groups include, but are not limited to, ethenyl, propenyl, n-butenyl, and i-butenyl.

The term "lower alkynyl" means an aliphatic hydrocarbon group containing one or more carbon-carbon triple bonds and which may be straight or branched having 2 to about 10 carbon atoms in the chain. In one embodiment, the alkynyl groups have 2 to about 4 carbon atoms in the chain. Branched means that one or more lower alkyl groups such as methyl, ethyl, or propyl are attached to a linear alkynyl chain. Representative alkynyl groups include, but are not limited to, ethynyl, propynyl, n-butynyl, 2-butynyl, 3-methylbutynyl, and n-pentynyl.

The term "lower alkoxyl" means a lower alkyl group defined above that bonds to an oxygen. Representative alkoxyl groups include, but are not limited to, methoxy, ethoxy, and propyloxy.

The term "3 to 10-membered carbocycle" means a monocyclic or bicyclic non-aromatic or aromatic ring system with 3-10 carbon atoms. Representative non-aromatic carbocycles include, but are not limited to, cyclopropyl, cyclobutyl, cyclopentyl, cylcohexyl, and cycloheptyl. Representative aromatic carbocycles include, but are not limited to, phenyl, naphthyl, indanyl, and indenyl.

The term "3 to 10-membered heterocycle" means a monocyclic or bicyclic non-aromatic or aromatic ring system with 3-10 atoms, of which at least one ring atom is O, S, or N.

Representative heterocycles include, but are not limited to, aziridinyl, azetidinyl, pyrrolidinyl, piperidinyl, azepanyl, 1,4-diazepanyl, tetrahydrofuranyl, tetrohydropyranyl, piperazinyl, morpholinyl, thiomorpolinyl, pyridyl, 2-oxo-pyridin-1(2H)-yl, pyrimidinyl, pyridazinyl, 6-oxopyridazin-1(6H)-yl, pyrazinyl, triazinyl, pyranyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydrobenzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3-dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and 3-thio-[1,2,4]triazolo[4,3-a]pyridin-2(3H)-yl.

The term "substituted" or "substitution" of an atom means that one or more hydrogen on the designated atom is replaced with a selection from the indicated group, provided that the designated atom's normal valency is not exceeded. "Unsubstituted" atoms bear all of the hydrogen atoms dictated by their valency. When a substituent is oxo or thio (i.e., =O or =S), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "compounds of the invention", and equivalent expressions, are meant to embrace compounds of general formulae (I), (II), and/or (III) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Representative acid addition salts include, but are not limited to, the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzene-sulphonates, p-toluenesulphonates, cyclohexylsulphamates, and quinateslaurylsulphonate salts. (See, for example, Berge et al., $J.$ $Pharm.$ $Sci.$ 66:1-sup.19 (1977) and $Remington's$ $Pharmaceutical$ $Sciences,$ 17th ed, p. 1418, Mack Publishing Company, Easton, Pa. (1985), which are hereby incorporated by reference in their entirety). Base addition salts can also be prepared by separately reacting the purified compound in its acid form with a suitable organic or inorganic base and isolating the salt thus formed. Base addition salts include, but are not limited to, pharmaceutically acceptable metal and amine salts. Suitable metal salts include, but are not limited to, the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, and zinc hydroxide. Suitable amine base addition salts are prepared from amines which have sufficient basicity to form a stable salt, and include, but are not limited to, the following amines which are frequently used in medicinal chemistry because of their low toxicity and acceptability for medical use: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Bundgaard, ed., *Design of Prodrugs*, Elsevier (1985); Widder et al., *Methods in Enzymology*, ed., Academic Press, 42:309-396 (1985); "Design and Applications of Prodrugs," Krogsgaard-Larsen, ed., *A Textbook of Drug Design and Development*, Chapter 5:113-191 (1991); Bundgaard, *Adv. Drug Del. Rev.* 8:1-38 (1992); Bundgaard et al., *J. Pharm. Sci.* 77:285 (1988); Nakeya et al., *Chem. Pharm. Bull.* 32:692 (1984); Higuchi, "Pro-drugs as Novel Delivery Systems" Roche, ed., A.C.S. Symposium Series, Vol. 14, and "Bioreversible Carriers in Drug Design" American Pharmaceutical Association and Pergamon Press (1987), which are hereby incorporated by reference in their entirety. Examples of prodrugs include, but are not limited to, acetate, formate, and benzoate derivatives of alcohol and amine functional groups in the compounds of the invention.

The term "therapeutically effective amount" is meant to describe an amount of compound of the present invention effective in inhibiting sodium dependent glucose co-transporters and thus producing the desired therapeutic effect. Such amounts generally vary according to a number of factors well within the purview of ordinarily skilled artisans given the description provided herein to determine and account for. These include, without limitation: the particular subject, as well as its age, weight, height, general physical condition and medical history, the particular compound used, as well as the carrier in which it is formulated and the route of administration selected for it; and, the nature and severity of the condition being treated.

The term "pharmaceutical composition" means a composition comprising compounds of formulae (I), (II), and/or (III) and at least one component selected from pharmaceutically acceptable carriers, diluents, adjuvants, excipients, and vehicles, such as preserving agents, fillers, disintegrating agents, wetting agents, emulsifying agents, suspending agents, sweetening agents, flavoring agents, perfuming agents, antibacterial agents, antifungal agents, lubricating agents, and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin. Examples of suitable carriers, diluents, solvents or vehicles include water, ethanol, polyols, suitable mixtures thereof, vegetable oils (such as olive oil) and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules and suppositories, as well as liquid preparations for injections, including liposome preparations. Techniques and formulations generally may be found in Remington's Pharmaceutical Sciences, 17th ed, Easton, Pa., Mack Publishing Company (1985), which is hereby incorporated by reference in its entirety.

Specific compounds of formula (I) of the present invention include, but are not limited to, the following compounds:

2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-6-methyl-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-7-(trifluoromethyl)-[1,2,4]triazolo[4,3-a]pyridin-3(2H)-one;

7-chloro-2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-6-(trifluoromethyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-6-(hydroxymethyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-a]pyridine-3(2H)-thione;

6-chloro-2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-7-methyl-[1,2,4]triazolo[4,3-a]pyridin-3(2H)-one;

6-bromo-2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-6-fluoro-[1,2,4]triazolo[4,3-a]pyridin-3(2H)-one;

6-chloro-2-(2-chloro-5-((2S,3R,4R,5S,6R)-3,4,5-trihydroxy-6-(hydroxymethyl)tetrahydro-2H-pyran-2-yl)benzyl)-7-methyl-[1,2,4]triazolo[4,3-a]pyridin-3(2H)-one;

1-(2-(2-chloro-5-((2S,3R,4R,5S,6R)-3,4,5-trihydroxy-6-(hydroxymethyl)tetrahydro-2H-pyran-2-yl)benzyl)-3-oxo-2,3-dihydro-[1,2,4]triazolo[4,3-a]pyridin-6-yl)cyclopropanecarbonitrile;

2-(2-chloro-5-((2S,3R,4R,5S,6R)-3,4,5-trihydroxy-6-(hydroxymethyl)tetrahydro-2H-pyran-2-yl)benzyl)-7-(hydroxymethyl)-[1,2,4]triazolo[4,3-a]pyridin-3(2H)-one;

2-(2-chloro-5-((2S,3R,4R,5S,6R)-3,4,5-trihydroxy-6-(hydroxymethyl)tetrahydro-2H-pyran-2-yl)benzyl)-6-(2-hydroxyethyl)-[1,2,4]triazolo[4,3-a]pyridin-3(2H)-one.

Specific compounds of formula (II) of the present invention include, but are not limited to, the following compounds:
(2S,3R,4R,5S,6R)-2-(3-([1,2,4]triazolo[1,5-a]pyridin-6-ylmethyl)-4-chlorophenyl)-6-(hydroxymethyl)tetrahydro-2H-pyran-3,4,5-triol; and 5-(2-chloro-5-((2S,3R,4R,5S,6R)-3,4,5-trihydroxy-6-(hydroxymethyl)tetrahydro-2H-pyran-2-yl)benzyl)furo[3,2-c]pyridin-4(5H)-one.

One embodiment of the present invention relates to the compound of formula (II) with the proviso that when X is

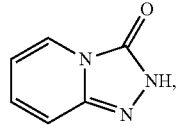

X can only be attached to the carbon designated * in formula (II) via a carbon atom or a ring carbon atom on X.

Another embodiment of the present invention relates to the compound of formula (III) wherein:
Y is

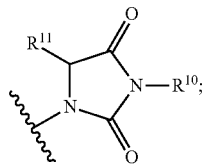

$R^5$ is Cl;
$R^6$, $R^7$, and $R^8$ are all H;
$R^9$ is $CH_2OH$;
$R^{10}$ is methyl, ethyl, or isopropyl; and
$R^{11}$ is H, methyl, ethyl, or gem-dimethyl.

A further embodiment of the present invention relates to the compound of formula (III) wherein:
Y is

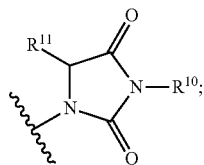

$R^5$ is Cl;
$R^6$, $R^7$, and $R^8$ are all H;
$R^9$ is $CH_2OH$;
$R^{10}$ is methyl, ethyl, or isopropyl; and
$R^{11}$ is H.

Another embodiment of the present invention relates to the compound of formula (III) wherein:
Y is

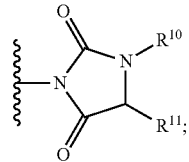

$R^5$ is Cl;
$R^6$, $R^7$, and $R^8$ are all H;
$R^9$ is $CH_2OH$;
$R^{10}$ is H, lower alkyl, lower alkenyl, or lower alkynyl, wherein each lower alkyl, lower alkenyl, or lower alkynyl is optionally substituted 1-3 times by $R^e$ as defined above; and
$R^{11}$ is H, methyl, ethyl, or gem-dimethyl.

Specific compounds of formula (III) of the present invention include, but are not limited to, the following compounds:

1-(4-(2-chloro-5-((2S,3R,4R,5S,6R)-3,4,5-trihydroxy-6-(hydroxymethyl)tetrahydro-2H-pyran-2-yl)benzyl)phenyl)-3,5,5-trimethylimidazolidine-2,4-dione;

1-(4-(2-chloro-5-((2S,3R,4R,5S,6R)-3,4,5-trihydroxy-6-(hydroxymethyl)tetrahydro-2H-pyran-2-yl)benzyl)phenyl)-3-isopropylimidazolidine-2,4-dione;

1-(4-(2-chloro-5-((2S,3R,4R,5S,6R)-3,4,5-trihydroxy-6-(hydroxymethyl)tetrahydro-2H-pyran-2-yl)benzyl)phenyl)-3-propylimidazolidine-2,4-dione;

1-(4-(2-chloro-5-((2S,3R,4R,5S,6R)-3,4,5-trihydroxy-6-(hydroxymethyl)tetrahydro-2H-pyran-2-yl)benzyl)phenyl)-3-methylimidazolidine-2,4-dione;

1-(4-(2-chloro-5-((2S,3R,4R,5S,6R)-3,4,5-trihydroxy-6-(hydroxymethyl)tetrahydro-2H-pyran-2-yl)benzyl)phenyl)imidazolidine-2,4-dione;

1-(4-(2-chloro-5-((2S,3R,4R,5S,6R)-3,4,5-trihydroxy-6-(hydroxymethyl)tetrahydro-2H-pyran-2-yl)benzyl)phenyl)-3-ethylimidazolidine-2,4-dione;

1-(4-(2-chloro-5-((2S,3R,4R,5S,6R)-3,4,5-trihydroxy-6-(hydroxymethyl)tetrahydro-2H-pyran-2-yl)benzyl)phenyl)-3-tritylimidazolidine-2,4-dione;

3-(4-(2-chloro-5-((2S,3R,4R,5S,6R)-3,4,5-trihydroxy-6-(hydroxymethyl)tetrahydro-2H-pyran-2-yl)benzyl)phenyl)-1-methylimidazolidine-2,4-dione;

3-(4-(2-chloro-5-((2S,3R,4R,5S,6R)-3,4,5-trihydroxy-6-(hydroxymethyl)tetrahydro-2H-pyran-2-yl)benzyl)phenyl)imidazolidine-2,4-dione;

3-(4-(2-chloro-5-((2S,3R,4R,5S,6R)-3,4,5-trihydroxy-6-(hydroxymethyl)tetrahydro-2H-pyran-2-yl)benzyl)phenyl)-1-ethylimidazolidine-2,4-dione;

3-(4-(2-chloro-5-((2S,3R,4R,5S,6R)-3,4,5-trihydroxy-6-(hydroxymethyl)tetrahydro-2H-pyran-2-yl)benzyl)phenyl)-1-isopropylimidazolidine-2,4-dione; and 3-(4-(2-chloro-5-((2S,3R,4R,5S,6R)-3,4,5-trihydroxy-6-(hydroxymethyl)tetrahydro-2H-pyran-2-yl)benzyl)phenyl)-1-propylimidazolidine-2,4-dione.

Within these embodiments, the selection of a particular preferred substituent at any one of $R^1$-$R^{11}$ and $R^a$-$R^h$ does not affect the selection of a substituent at any of the others of $R^1$-$R^{11}$ and $R^a$-$R^h$. That is, preferred compounds provided herein have any of the preferred substituents at any of the positions.

One embodiment of the present invention relates to pharmaceutically acceptable salts, or non-salt forms, of any of the compounds of formula (I), (II), or (III) described herein.

Single enantiomers, any mixture of enantiomers, including racemic mixtures, or diastereomers (both separated and as any mixtures) of the compounds of the present invention are also included within the scope of the invention.

The scope of the present invention also encompasses active metabolites of the present compounds.

The present invention also includes compounds of formula (I), (II), or (III), wherein one or more of the atoms, e.g., C or H, are replaced by the corresponding radioactive isotopes of that atom (e.g., C replaced by $^{14}C$ and H replaced by $^{3}H$), or a stable isotope of that atom (e.g., C replaced by $^{13}C$ or H replaced by $^{2}H$). Radioisotopes of hydrogen, carbon, phosphorous, fluorine, iodine and chlorine include $^{3}H$, $^{14}C$, $^{35}S$, $^{18}F$, $^{32}P$, $^{33}P$, $^{125}I$, and $^{36}Cl$, respectively. Compounds that contain those radioisotopes and/or other radioisotopes of other atoms are within the scope of this invention. Radiolabeled compounds described herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent. Such compounds have a variety of potential uses, e.g., as standards and reagents in determining the ability of a potential pharmaceutical to inhibit SGLTs. In addition, in the case of stable isotopes, such compounds may have the potential to favorably modify the biological properties, e.g., pharmacological and/or pharmacokinetic properties, of compounds of formula (I), (II), or (III). The details concerning selection of suitable sites for incorporating radioactive isotopes into the compounds are known to those skilled in the art.

Compounds of the present invention as described herein are useful as SGLT inhibitors. It may be found upon examination that compounds that are not presently excluded from the claims are not patentable to the inventors in this application. In that case, the exclusion of species and genera in applicants' claims are to be considered artifacts of patent prosecution and not reflective of the inventors' concept or description of their invention. The invention, in a compound aspect, is all compounds of formula (I), (II), and (III), except those that are in the public's possession.

While it may be possible for compounds of formula (I), (II), and (III) to be administered as the raw chemical, it will sometimes be preferable to present them as part of a pharmaceutical composition. Accordingly, another aspect of the present invention is a pharmaceutical composition containing a therapeutically effective amount of a compound of formula (I), (II), or (III), or a pharmaceutically acceptable salt or solvate thereof, and a pharmaceutically acceptable carrier. The carrier must be "acceptable" in the sense of being compatible with the other ingredients of the formulation and not deleterious to the recipient thereof. Furthermore, when reference is made in an independent claim to a compound or a pharmaceutically acceptable salt thereof, it will be understood that claims which depend from that independent claim which refer to such a compound also include pharmaceutically acceptable salts of the compound, even if explicit reference is not made to the salts.

Another aspect of the present invention relates to a method of treating a disease or condition which is susceptible to treatment with a SGLT inhibitor. This method involves selecting a patient with a disease or condition which is susceptible to treatment with a SGLT inhibitor and administering to the patient a therapeutically effective amount of a compound of formula (I), (II), or (III) or a pharmaceutically acceptable salt thereof.

The pharmaceutical composition according to the present invention can be administered to mammals, preferably humans, for the treatment of a variety of diseases or conditions which are susceptible to treatment with a SGLT inhibitor in accordance with the present invention including, but not limited to, diabetes (including Type I and Type II, impaired glucose tolerance, insulin resistance, and diabetic complications, such as retinopathy, nephropathy, neuropathy, and cataracts), hyperglycemia, hyperinsulinemia, hyperchlolesterolemia, elevated blood level of free fatty acids or glycerol, hyperlipidemia, hypertriglyceridemia, obesity, wound healing, tissue ischemia, atherosclerosis, and hypertension. The compounds of the present invention and/or pharmaceutical compositions employing these compounds may also be utilized to increase the blood levels of high density lipoprotein (HDL). These compounds and compositions are also useful for treating and preventing kidney stones, hyperuricemia, and gout. These compounds and compositions are also useful for treating hyponatremia.

In addition, the condition, diseases, and maladies collectively referred to as "Syndrome X" or Metabolic Syndromeas detailed in Johannsson et al., *J. Clin. Endocrinol. Metab* 82:727-734 (1997) which is hereby incorporated by reference in its entirety, may be treated using the compounds of the present invention.

Where desired, the compound of formulae (I), (II), or (III) can be administered with one or more other types of therapeutic adjuncts, such as antidiabetic agents, which may be administrated orally in the same dosage form, in a separate oral dosage form, or by injection. Suitable types of antidiabetic agents include, but are not limited to, biguandies such as metformin, sulfonyl ureas, PPAR γ agonists, glucosidase inhibitors, DPP IV inhibitors, GLP-1 agonists, amylin, and insulin.

The present invention also relates to methods of making compounds of formulae (I), (II), and (III). In one embodiment, the present invention relates to a process for preparation of a product compound of formula (I) comprising treating an intermediate compound of formula IA

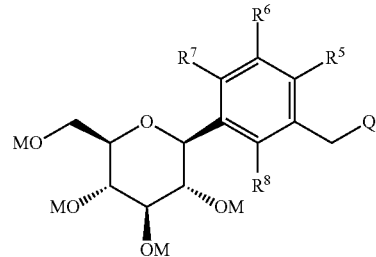

IA wherein M is acetyl, para-methoxybenzyl, or methoxylmethyl and Q is halogen or OH, under conditions effective to produce the product compound. Treating may include reacting the intermediate compound of formula IA with an intermediate compound of formula IB

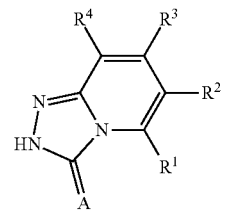

IB under conditions effective to produce the product compound.

Another embodiment of the present invention relates to a process for preparation of a product compound of formula (II) comprising treating an intermediate compound of formula IA

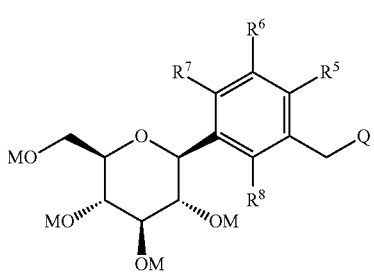

IA wherein M is acetyl, para-methoxybenzyl, or methoxylmethyl and Q is halogen or OH, under conditions effective to produce the product compound.

Yet another embodiment of the present invention relates to a process for preparation of a product compound of formula (III) comprising treating an intermediate compound of formula IA

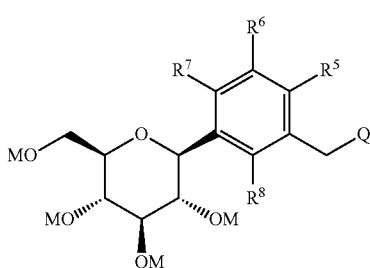

IA wherein M is acetyl, para-methoxybenzyl, or methoxylmethyl and Q is Cl, Br, or I, under conditions effective to produce the product compound.

In accordance with this embodiment, treating may comprise reacting the intermediate compound of formula IA with an intermediate compound of formula IIIB

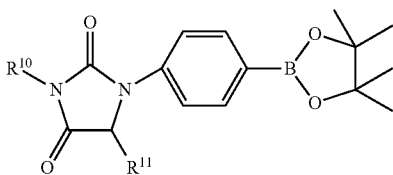

IIIB under conditions effective to produce the product compound.

In accordance with this embodiment, treating may comprise reacting the intermediate compound of formula IA with an intermediate compound of formula IIIC

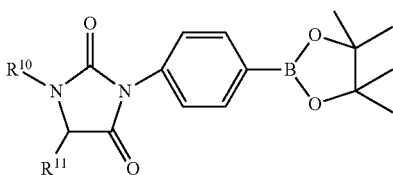

IIIC under conditions effective to produce the product compound.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

Compounds according to the invention, for example, starting materials, intermediates, or products, are prepared as described herein or by the application or adaptation of known methods, by which is meant methods used heretofore or described in the literature, for example, those described by Larock, *Comprehensive Organic Transformations*, Wiley-VCH publishers, New York (1989), which is hereby incorporated by reference in its entirety.

A compound of formula (I), (II), or (III) including a group containing one or more nitrogen ring atoms, may be converted to the corresponding compound wherein one or more nitrogen ring atom of the group is oxidized to an N-oxide, preferably by reacting with a peracid, for example peracetic acid in acetic acid or m-chloroperoxybenzoic acid in an inert solvent such as dichloromethane, at a temperature from about room temperature to reflux, preferably at elevated temperature.

In the reactions described hereinafter, it may be necessary to protect reactive functional groups, for example hydroxy, amino, imino, thio, or carboxy groups, where these are desired in the final product, to avoid their unwanted participation in the reactions. Conventional protecting groups may be used in accordance with standard practice.

The novel SGLT inhibitors of formulae (I), (II), and (III) of this invention can be prepared by the methods illustrated in the representative reaction schemes as, for example, described below, or by modifications thereof, using readily available starting materials, reagents, and conventional synthesis procedures. In these reactions, it is also possible to make use of variants that are known in the art but are not mentioned here. Although the syntheses depicted herein may result in the preparation of stereoisomers having a particular stereochemistry, included within the scope of the present invention are compounds of formula (I), (II), and (III) in any stereoisomeric form, and preparation of compounds of formula (I), (II), and (III) in stereoisomeric forms other than those depicted herein would be obvious to one of ordinary skill in the chemical arts based on the procedures presented herein.

The synthesis of compounds of formulae (I) and (II) (where X is connected to the carbon designated * in formula (II) via a ring nitrogen atom on X) is exemplified in the following Scheme 1:

Scheme 1

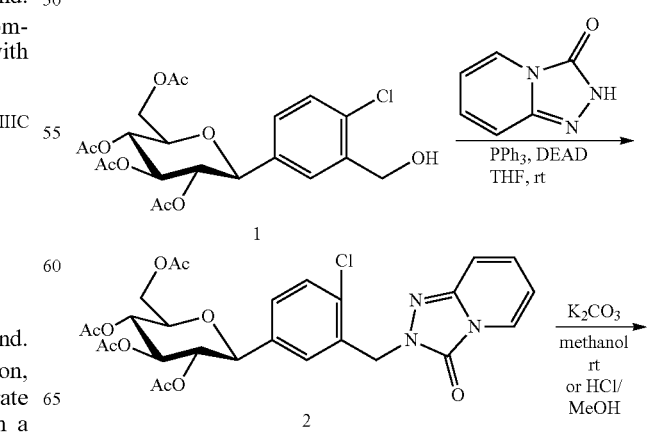

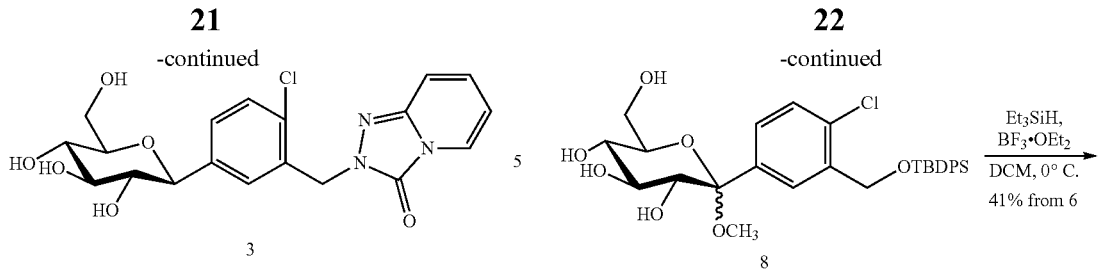

Compound 1 was prepared according to the teaching in US Published Patent Application No. 2005/0233988 to Nomuro et al. which is hereby incorporated by reference in its entirety. A Mitsunobu reaction gave compound 2 which was converted to compound 3 after removing the acetyl groups.

Alternatively, compound 3 can be prepared as depicted in Scheme 2. In particular, compound 4 and [1,2,4]triazolo[4,3-a]pyridin-3(2H)-one was treated with sodium hydride in DMF to give compound 5 which was then deprotected to yield compound 3.

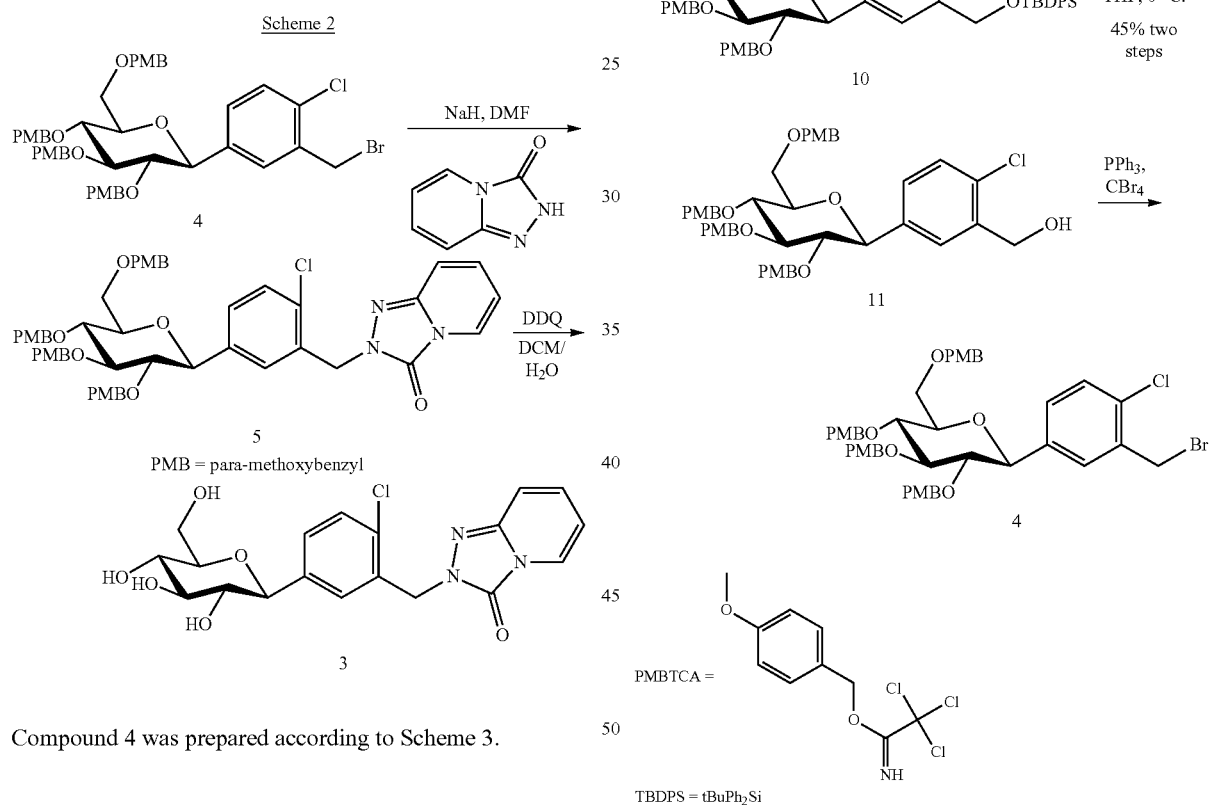

Compound 4 was prepared according to Scheme 3.

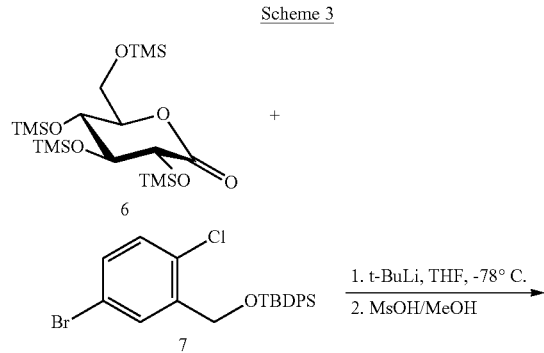

Another alternative method to prepare compounds of formulae (I) and (II) when $R^7$=OMe is exemplified in Scheme 4. Acetyl protected glucose and 4-methoxytoluene reacted under Lewis acid conditions gave compound 12 as the preferred anomer (Kuribayashi et al., "Bis C-Glycosylated Diphenylmethanes for Stable Glycoepitope Mimetics," *Synlett* 6:737-740 (1999), which is hereby incorporated by reference in its entirety). Benzylic bromination afforded compound 13 which underwent alkylation with 6-chloro-[1,2,4]triazolo[4,3-c]pyridin-3(2H)-one. Compound 14 was obtained after a deprotection procedure using potassium carbonate.

Scheme 4

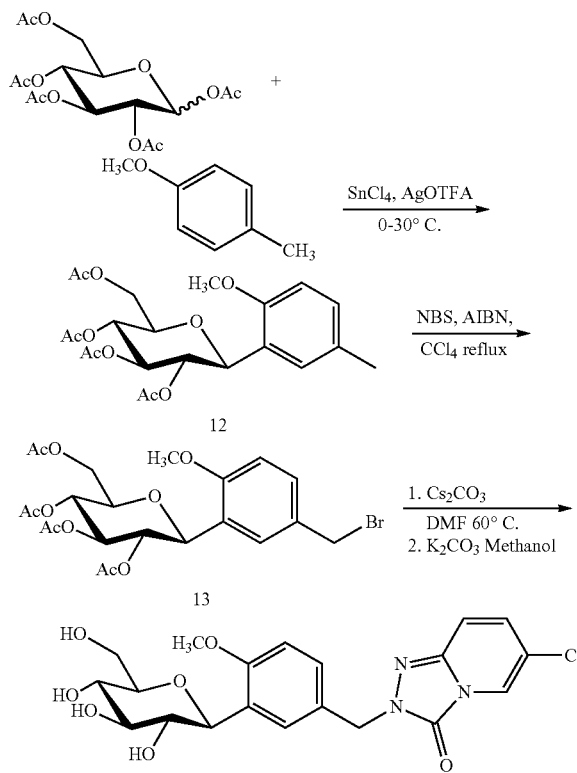

The oxo-triazolopyridine VI can be prepared from substituted pyridine IV as depicted in Scheme 5 using well known methods. Many compounds of formula VI are also commercially available.

Scheme 5

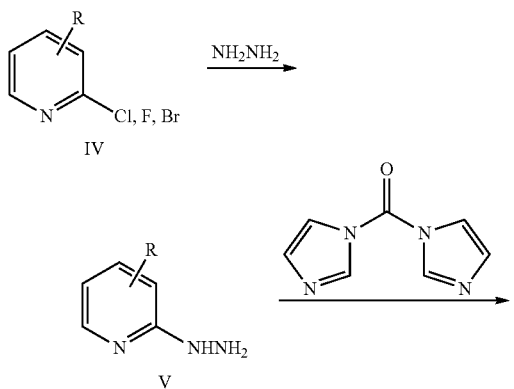

The synthesis of compounds of formula (II) (connecting through the atom of X) is exemplified by the synthesis of compound 1 as depicted in Scheme 6. In particular, compound 15 underwent a palladium-mediated cross-coupling with compound 18 to give compound 16 which was then deprotected to afford compound 17.

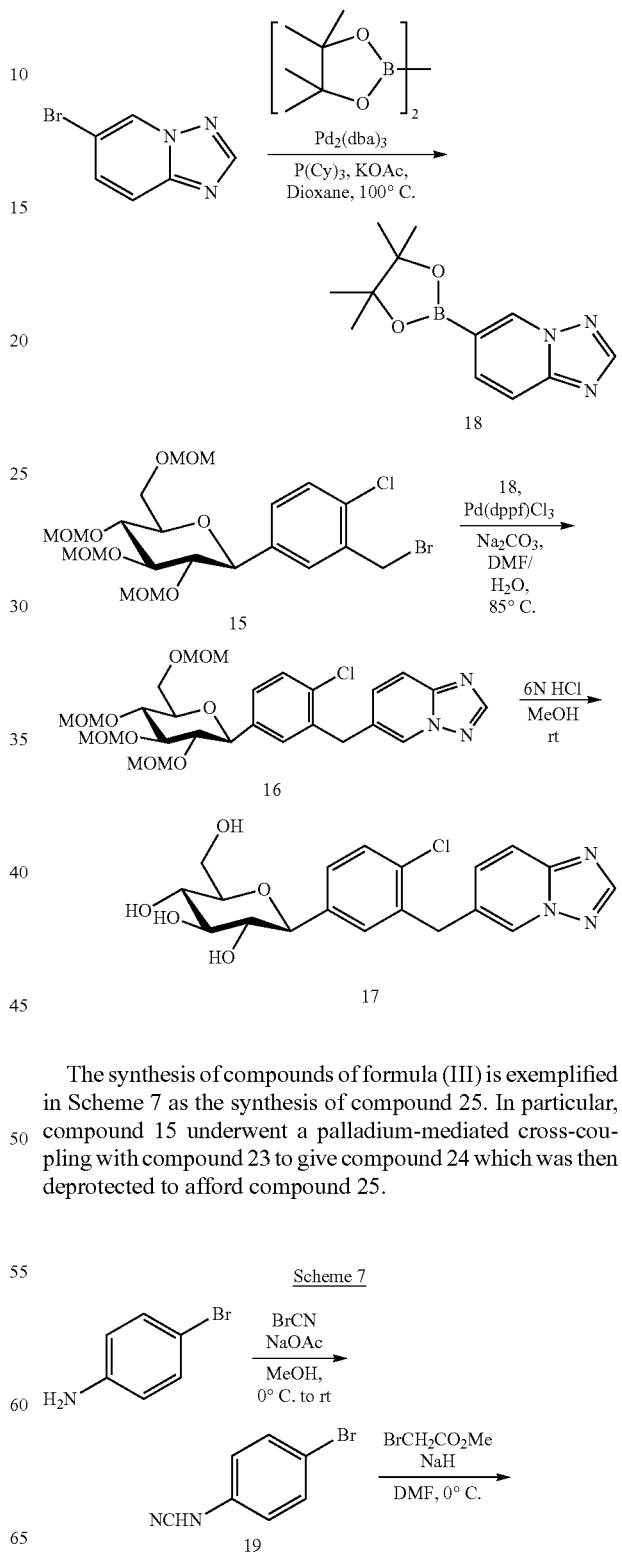

The synthesis of compounds of formula (III) is exemplified in Scheme 7 as the synthesis of compound 25. In particular, compound 15 underwent a palladium-mediated cross-coupling with compound 23 to give compound 24 which was then deprotected to afford compound 25.

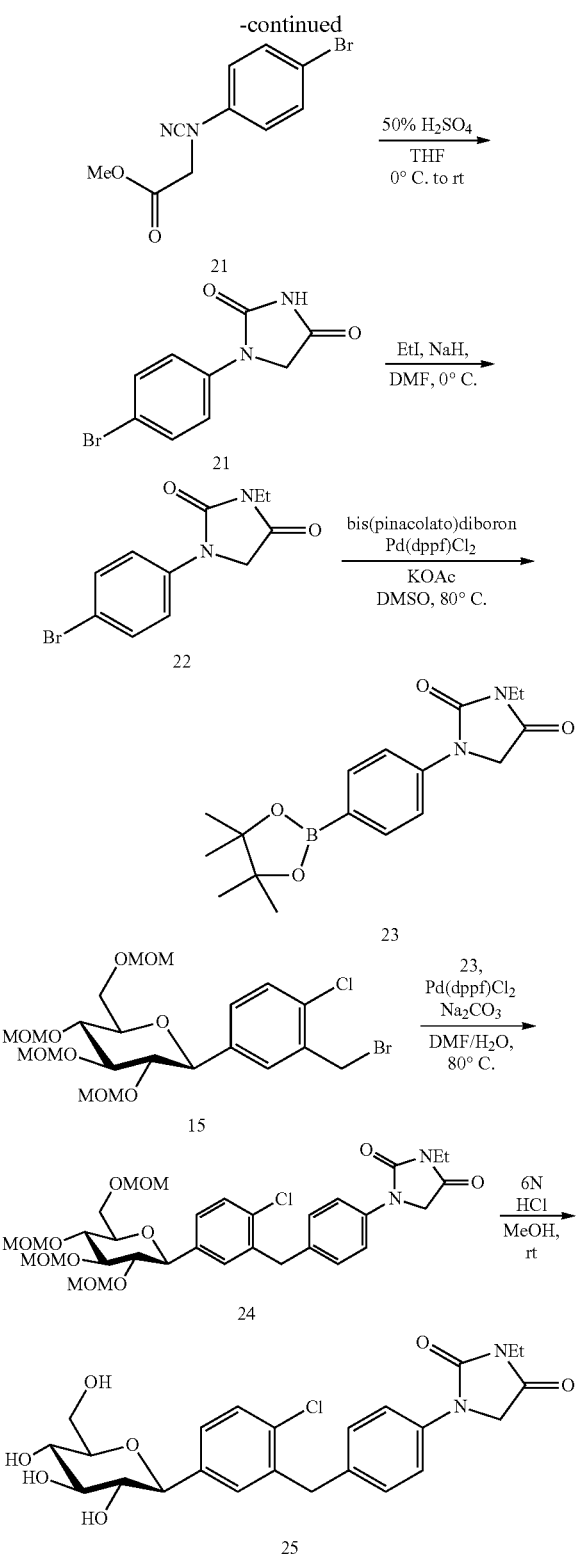

It will be appreciated that compounds according to the present invention contain asymmetric centers. These asymmetric centers may independently be in either the R or S configuration and such compounds are able to rotate a plane of polarized light in a polarimeter. If said plane of polarized light is caused by the compound to rotate in a counterclockwise direction, the compound is said to be the (−) stereoisomer of the compound. If said plane of polarized light is caused by the compound to rotate in a clockwise direction, the compound is said to be the (+) stereoisomer of the compound. It will be apparent to those skilled in the art that certain compounds useful according to the invention may also exhibit geometrical isomerism. It is to be understood that the present invention includes individual geometrical isomers and stereoisomers and mixtures thereof, including racemic mixtures, of compounds of formulae (I), (II), and/or (III) herein above. Such isomers can be separated from their mixtures, by the application or adaptation of known methods, for example chromatographic techniques and recrystallization techniques, or they are separately prepared from the appropriate isomers of their intermediates.

Radiolabeled compounds of the invention are synthesized by a number of techniques well-known to those of ordinary skill in the art, e.g., by using starting materials incorporating therein one or more radioisotopes. Compounds of the present invention where a stable radioisotope, such as carbon-14, tritium, iodine-121, or another radioisotope, has been introduced synthetically are useful diagnostic agents.

The present invention provides compositions containing the compounds described herein, including, in particular, pharmaceutical compositions comprising therapeutically effective amounts of the compounds and pharmaceutically acceptable carriers.

It is a further object of the present invention to provide kits having a plurality of active ingredients (with or without carrier) which, together, may be effectively utilized for carrying out the novel combination therapies of the invention.

It is another object of the invention to provide a novel pharmaceutical composition which is effective, in and of itself, for utilization in a beneficial combination therapy because it includes a plurality of active ingredients which may be utilized in accordance with the invention.

The present invention also provides kits or single packages combining two or more active ingredients useful in treating the disease. A kit may provide (alone or in combination with a pharmaceutically acceptable diluent or carrier) the compounds of formulae (I), (II), and/or (III), and an additional active ingredient (alone or in combination with diluent or carrier), such as biguandies, sulfonyl ureas, PPAR γ agonists, glucosidase inhibitors, DPP IV inhibitors, GLR-1 agonists, amylin, and insulin.

The formulations of compounds of formula (I), (II), or (III) include those suitable for oral, parenteral (including subcutaneous, intradermal, intramuscular, intraperitoneal, intravenous, and intraarticular), rectal, colonic, and topical (including dermal, buccal, nasal, sublingual, and intraocular) administration. The most suitable route may depend upon the condition and disorder of the recipient. The formulations may conveniently be presented in unit dosage form and may be prepared by any of the methods well known in the art of pharmacy. Such methods include the step of bringing into association a compound of formula (I), (II), or (III), or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

The compounds according to the present invention may be presented in forms permitting administration by the most suitable route and the invention also relates to pharmaceutical compositions containing at least one compound according to the invention which are suitable for use in human or veterinary medicine. These compositions may be prepared according to the customary methods, using one or more pharmaceutically acceptable adjuvants or excipients. The adjuvants comprise, inter alia, diluents, sterile aqueous media, and the various non-toxic organic solvents. The compositions may be presented in the form of tablets, pills, granules, powders, aqueous solutions or suspensions, injectable solutions, elixirs or syrups, and can contain one or more agents chosen from the group comprising sweeteners, flavorings, colorings, or stabilizers in order to obtain pharmaceutically acceptable preparations.

The choice of vehicle and the content of active substance in the vehicle are generally determined in accordance with the solubility and chemical properties of the product, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulfate, and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol, and chloroform or mixtures thereof may also be used.

Formulations suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary, or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active, or dispersing agent. Molded tablets may be made by molding in a suitable machine a mixture of the powdered compound moistened with an inert liquid diluent. The tablets may optionally be coated or scored and may be formulated so as to provide sustained, delayed, or controlled release of the active ingredient therein. The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Pharmaceutical compositions may also optionally include other therapeutic ingredients, anti-caking agents, preservatives, sweetening agents, colorants, flavors, desiccants, plasticizers, dyes, and the like. Any such optional ingredient must be compatible with the compound of formula (I), (II), or (III) to insure the stability of the formulation. The composition may contain other additives as needed, including for example lactose, glucose, fructose, galactose, trehalose, sucrose, maltose, raffinose, maltitol, melezitose, stachyose, lactitol, palatinite, starch, xylitol, mannitol, myoinositol, and the like, and hydrates thereof, and amino acids, for example alanine, glycine and betaine, and peptides and proteins, for example albumen.

Examples of excipients for use as the pharmaceutically acceptable carriers and the pharmaceutically acceptable inert carriers and the aforementioned additional ingredients include, but are not limited to binders, fillers, disintegrants, lubricants, anti-microbial agents, and coating agents.

The dose range for adult humans is generally from 0.001 mg to 10 g/day orally. Tablets or other forms of presentation provided in discrete units may conveniently contain an amount of compound of formula (I), (II), or (III) which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity.

For additional information about pharmaceutical compositions and their formulation, see, for example, *Remington, The Science and Practice of Pharmacy*, 20$^{th}$ Edition (2000), which is hereby incorporated by reference in its entirety.

The compounds of formula (I), (II), or (III) can be administered, e.g., by intravenous injection, intramuscular injection, subcutaneous injection, intraperitoneal injection, topical, sublingual, intraarticular (in the joints), intradermal, buccal, ophthalmic (including intraocular), intranasally (including using a cannula), or by other routes. The compounds of formula (I), (II), or (III) can be administered orally, e.g., as a tablet or cachet containing a predetermined amount of the active ingredient, gel, pellet, paste, syrup, bolus, electuary, slurry, capsule, powder, granules, as a solution or a suspension in an aqueous liquid or a non-aqueous liquid, as an oil-in-water liquid emulsion or a water-in-oil liquid emulsion, via a micellar formulation (see, e.g. PCT Publication No. WO 97/11682, which is hereby incorporated by reference in its entirety) via a liposomal formulation (see, e.g., European Patent EP 736299 and PCT Publication Nos. WO 99/59550 and WO 97/13500, which are hereby incorporated by reference in their entirety), via formulations described in PCT Publication No. WO 03/094886, which is hereby incorporated by reference in its entirety, or in some other form. The compounds of formula (I), (II), or (III) can also be administered transdermally (i.e. via reservoir-type or matrix-type patches, microneedles, thermal poration, hypodermic needles, iontophoresis, electroporation, ultrasound or other forms of sonophoresis, jet injection, or a combination of any of the preceding methods (Prausnitz et al., *Nature Reviews Drug Discovery* 3:115 (2004), which is hereby incorporated by reference in its entirety)).

Suitable compositions containing the compounds of the present invention may be prepared by conventional means. For example, compounds of the present invention may be dissolved or suspended in a suitable carrier for use in a nebulizer or a suspension or solution aerosol, or may be absorbed or adsorbed onto a suitable solid carrier for use in a dry powder inhaler.

Solid compositions for rectal administration include suppositories formulated in accordance with known methods and containing at least one compound of formula (I), (II), or (III).

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.5 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product. A dosage unit (e.g. an oral dosage unit) can include from, for example, 0.01 to 0.1 mg, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 0.01 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg) of a compound described herein.

Compounds of formula (I), (II), or (III) can be incorporated into a liposome to improve half-life. Compounds of formula (I), (II), or (III) can also be conjugated to polyethylene glycol (PEG) chains. Methods for pegylation and additional formulations containing PEG-conjugates (i.e. PEG-based hydrogels, PEG modified liposomes) can be found in Harris et al., *Nature Reviews Drug Discovery*, 2:214-221 (2003) and the references therein, which are hereby incorporated by reference in their entirety. Compounds of formula (I), (II), or (III) can also be administered via a nanocochleate or cochleate delivery vehicle (BioDelivery Sciences International, Raleigh, N.C.). Compounds of formula (I), (II), or (III) can also be delivered using nanoemulsion formulations.

The compounds according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active compound may be administered orally 1 to 4 times per day. It goes without saying that, for other patients, it will be necessary to prescribe not more than one or two doses per day.

EXAMPLES

The Examples set forth below are for illustrative purposes only and are not intended to limit, in any way, the scope of the present invention.

Unless otherwise noted, reagents and solvents were used as received from commercial suppliers. Proton nuclear magnetic resonance (NMR) spectra were obtained on Bruker spectrometers at 300, 400, or 500 MHz. Spectra are given in ppm ($\delta$) and coupling constants, J, are reported in Hertz. Tetramethylsilane (TMS) was used as an internal standard. Mass spectra were collected using either a Finnigan LCQ Duo LCMS ion trap electrospray ionization (ESI) or a mass Varian 1200L single quadrapole mass spectrometer (ESI). High performance liquid chromatography (HPLC) analyses were obtained using a Luna C18(2) column (250×4.6 mm, Phenomenex) with UV detection at 254 nm or other suitable wavelengths using a standard solvent gradient program (Method A or Method B). If needed, Method A or Method B can be modified to achieve desired separation of compounds.

Method A:

| Time (min) | Flow (mL/min) | % A | % B |
|---|---|---|---|
| 0.0 | 1.0 | 90.0 | 10.0 |
| 20 | 1.0 | 10.0 | 90.0 |
| 25 | 1.0 | 10.0 | 90.0 |

A = Water with 0.025% Trifluoroacetic Acid
B = Acetonitrile with 0.025% Trifluoroacetic Acid Method B:

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |
| 31.0 | 1.0 | 90.0 | 10.0 |

A = Water with 0.05% Trifluoroacetic Acid
B = Acetonitrile with 0.05% Trifluoroacetic Acid Example 1

Preparation of 2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-a]pyridin-3(2H)-one According to Scheme 1

Step A: To a solution of (3R,4R,5R,6S)-2-(acetoxymethyl)-6-(4-chloro-3-(hydroxymethyl)phenyl)tetrahydro-2H-pyran-3,4,5-triyl triacetate (0.21 g, 0.43 mmol) and [1,2,4]triazolo[4,3-a]pyridin-3(2H)-one (67.4 mg, 0.50 mmol) in tetrahydrofuran (20 mL) were added triphenylphosphine (0.17 g, 0.65 mmol) and diethyl azodicarboxylate (0.11 g, 0.65 mmol) under nitrogen. The reaction solution was stirred at room temperature for 15 hours and then it was quenched with aqueous ammonium chloride solution, extracted with ethyl acetate. The organic extract was washed with brine, dried over sodium sulfate and concentrated in vacuo. The crude material was partially purified by flash column chromatography (eluent: hexanes/ethyl acetate 95:5 to 25:75) to give (3R,4R,5R,6S)-2-(acetoxymethyl)-6-(4-chloro-3-((3-oxo-[1,2,4]triazolo[4,3-a]pyridin-2(3H)-yl)methyl)phenyl)tetrahydro-2H-pyran-3,4,5-triyltriacetate (0.36 g, partial pure), which was used in the next step without further purification.

Step B: To a solution of the product from step A above (0.36 g, crude) in methanol (25 mL) was added potassium carbonate (0.17 g, 1.2 mmol). The reaction solution was stirred at room temperature for 18 hours and then it was concentrated in vacuo. The crude material obtained was purified by flash column chromatography (eluent: dichloromethane/methanol/concentrated ammonium hydroxide 98:1.8:0.2 to 80:18:2) to give 2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-c]pyridin-3(2H)-one (0.11 g, 55% over two steps; AUC HPLC 97.9%) as a white foam: $^1$H NMR (CD$_3$OD, 500 MHz) $\delta$ 7.86-7.84 (m, 1H), 7.41 (d, J=1.0 Hz, 2H), 7.37 (s, 1H), 7.25 (ddd, J=9.5, 6.5, 1.0 Hz, 1H), 7.15-7.12 (m, 1H), 6.68 (td, J=7.5, 1.0 Hz, 1H), 5.28 (s, 2H), 4.10 (d, J=9.5 Hz, 1H), 3.85 (dd, J=12.0, 1.5 Hz, 1H), 3.67

(dd, J=12.0, 5.5 Hz, 1H), 3.44-3.25 (m, 4H); ESI MS m/z 422 [M+H]$^+$. Anal. Calcd. for $C_{19}H_{20}ClN_3O_6 \cdot 1.25H_2O$: C, 51.36; H, 5.10; N, 9.46. Found: C, 51.23; H, 5.10; N, 9.48.

Example 2

Preparation of 2-(2-chloro-5-((2S,3R,4R,5S,6R)-3,4, 5-trihydroxy-6-(hydroxymethyl)tetrahydro-2H-pyran-2-yl)benzyl)-[1,2,4]triazolo[4,3-a]pyridin-3(2H)-one According to Scheme 3

Step A: To a solution of (3S,4S,5R)-3,4,5-tris(trimethylsilyloxy)-6-((trimethylsilyloxy)methyl)tetrahydro-2H-pyran-2-one (3.0 g, 6.5 mmol) and (5-bromo-2-chlorobenzyloxy)(tert-butyl)diphenylsilane (3.7 g, 7.8 mmol) in tetrahydrofuran (105 mL) at −78° C. under nitrogen was added t-BuLi (8.0 mL, 13.7 mmol) dropwise. Reaction was stirred at −78° C. for 5 hours and then a cold (−78° C.) solution of methanesulfonic acid (1.6 mL) in methanol (54 mL) was added to it via cannulation. The cold bath was then removed and the reaction mixture was stirred at room temperature overnight. The reaction solution was quenched with aqueous sodium bicarbonate and extracted with ethyl acetate (3×). The combined organic extract was washed with brine, dried over sodium sulfate and concentrated in vacuo to give (3S,4S,5S)-2-(3-((tert-butyldiphenylsilyloxy)methyl)-4-chlorophenyl)-6-(hydroxymethyl)-2-methoxytetrahydro-2H-pyran-3,4,5-triol (4.0 g, crude, mixture of 2 anomers at 2-position) as a white foam, which was used in the next step without purification.

Step B: To a solution of the product (3.5 g, crude) from step A in dichloromethane (60 mL) at 0° C. was added triethylsilane (3.1 mL, 19.4 mmol), followed by dropwise addition of boron trifluoride diethyl etherate (2.5 mL, 20.3 mmol). The reaction mixture was stirred at 0° C. for 2 hours and then it was quenched with aqueous sodium bicarbonate and extracted with ethyl acetate (3×). The combined organic extract was washed with brine, dried over sodium sulfate and concentrated in vacuo. The crude material obtained was purified by flash column chromatography (eluent: dichloromethane/methanol 99:1 to 93:7) to give (2S,3S,4R,5S)-2-(3-((tert-butyldiphenylsilyloxy)methyl)-4-chlorophenyl)-6-(hydroxymethyl)tetrahydro-2H-pyran-3,4,5-triol (1.45 g, 41% over two steps) as a white foam: $^1$H NMR (CD$_3$OD, 500 MHz) δ 7.81 (s, 1H), 7.71-7.69 (m, 4H), 7.45-7.39 (m, 6H), 7.34-7.26 (m, 2H), 4.81 (d, J=8.0 Hz, 2H), 4.16 (d, J=9.5 Hz, 1H), 3.91 (dd, J=11.5, 2.0 Hz, 1H), 3.69 (dd, J=12.0, 6.0 Hz, 1H), 3.50 (t, J=9.0 Hz, 1H), 3.47-3.42 (m, 1H), 3.39 (d, J=9.0 Hz, 1H), 3.37-3.32 (m, 1H), 1.11 (s, 9H).

Step C: To a solution of the product (0.62 g, 1.2 mmol) from step B and 4-methoxybenzyl-2,2,2-trichloroacetimidate (2.6 g, 9.2 mmol) in dichloromethane (8.0 mL) at room temperature was added camphorsulfonic acid (64 mg, 0.27 mmol). The reaction mixture was stirred at room temperature for 20 hours and then it was quenched with aqueous sodium bicarbonate and extracted with ethyl acetate (3×). The combined organic extract was washed with brine, dried over sodium sulfate and concentrated in vacuo. The crude material obtained was purified by flash column chromatography (eluent: hexanes/ethyl acetate 95:5 to 65:35) to give tert-butyl(2-chloro-5-((2S,3R,4R,5R)-3,4,5-tris(4-methoxybenzyloxy)-6-((4-methoxybenzyloxy)methyl)tetrahydro-2H-pyran-2-yl)benzyloxy)diphenylsilane (2.1 g, partial pure) as a semisolid, which was used in the next step without further purification.

Step D: To a solution of the product (2.1 g, crude) from step C in tetrahydrofuran (20.0 mL) at 0° C. was added tetrabutylammonium fluoride (2.0 mL, 1.0 M in THF). The reaction mixture was stirred at room temperature for 1 hour and then it was quenched with aqueous ammonium chloride and extracted with ethyl acetate (3×). The combined organic extract was washed with brine, dried over sodium sulfate and concentrated in vacuo. The crude material obtained was purified by flash column chromatography (eluent: hexanes/ethyl acetate 90:10 to 40:60) to give (2-chloro-5-((2S,3R,4R,5R)-3,4,5-tris(4-methoxybenzyloxy)-6-((4-methoxybenzyloxy)methyl)tetrahydro-2H-pyran-2-yl)phenyl)methanol (0.41 g, 45% over two steps): $^1$H NMR (CDCl$_3$, 500 MHz) δ 7.47 (d, J=2.0 Hz, 1H), 7.33-7.24 (m, 6H), 7.09 (d, J=8.5 Hz, 2H), 6.87-6.81 (m, 8H), 6.72 (d, J=8.5 Hz, 2H), 4.89-4.84 (m, 2H), 4.77 (d, J=10.5 Hz, 1H), 4.74-4.72 (m, 2H), 4.57-4.46 (m, 3H), 4.41 (d, J=10.5 Hz, 1H), 4.18 (d, J=9.5 Hz, 1H), 3.83-3.66 (m, 7H), 3.799 (s, 3H), 3.798 (s, 3H), 3.791 (s, 3H), 3.77 (s, 3H), 3.56-3.52 (m, 1H), 3.40 (t, J=9.0 Hz, 1H).

Step E: To a solution of the product from step D (0.36 g, 0.46 mmol) in tetrahydrofuran (5.0 mL) at 0° C. was added triphenylphosphine (0.36 g, 1.38 mmol), followed by dropwise addition of a solution of carbon tetrabromide (0.46 g, 1.38 mmol) in tetrahydrofuran (5.0 mL). The reaction mixture was allowed to warm to room temperature and stirred for 8 hours. The reaction solution was then quenched by addition of methanol and stirred for 15 minutes at room temperature. The resultant mixture was concentrated to dryness and the residue obtained was purified by flash column chromatography (eluent: hexanes/ethyl acetate 95:5 to 60:40) to give (2S,3R,4R,5R)-2-(3-(bromomethyl)-4-chlorophenyl)-3,4,5-tris(4-methoxybenzyloxy)-6-((4-methoxybenzyloxy)methyl)tetrahydro-2H-pyran (0.31 g, partial pure) as a light yellow oil, which was used in the next step without further purification.

Step F: To a suspension of sodium hydride (95.5 mg, 0.71 mmol) in DMF (2.0 mL) at 0° C. under nitrogen was added [1,2,4]triazolo[4,3-a]pyridin-3(2H)-one (33.6 mg, 0.84 mmol). The resultant solution was stirred at 0° C. for 5 minutes, then a solution of the product from step E (0.20 g, crude). The reaction mixture was let to warm to room temperature and stirred for 60 hours. Reaction was quenched with aqueous ammonium chloride and extracted with ethyl acetate. The organic extract was washed with water and brine, dried over sodium sulfate and concentrated in vacuo. The crude material obtained was then used in the next step without purification: LC-ESI MS m/z 902 [M+H]$^+$.

Step G: To a solution of the product from step F (0.18 g, 0.20 mmol) in a mixture of dichloromethane (4.0 mL) and water (0.20 mL) at room temperature was added DDQ (0.19 g, 0.85 mmol). The reaction solution was stirred at room temperature for 3 hours and then it was quenched with aqueous sodium bicarbonate and washed with dichloromethane and ethyl acetate. The organic extract was discarded and the aqueous layer was then extracted with a (3:1) mixture of chloroform/2-propanol (5×). The combined organic extract was dried over sodium sulfate and concentrated in vacuo. The crude material obtained was dissolved in a mixture of methanol and water and lyophilized overnight to give compound 2-(2-chloro-5-((2S,3R,4R,5S,6R)-3,4,5-trihydroxy-6-(hydroxymethyl)tetrahydro-2H-pyran-2-yl)benzyl)-[1,2,4]triazolo[4,3-c]pyridin-3(2H)-one.

Example 3

Preparation of 6-chloro-2-(4-methoxy-3-((2S,3R,4R, 5S,6R)-3,4,5-trihydroxy-6-(hydroxymethyl)tetrahydro-2H-pyran-2-yl)benzyl)-[1,2,4]triazolo[4,3-a]pyridin-3(2H)-one Step A: To a mixture of (3S,4S,5R)-6-(acetoxymethyl)tetrahydro-2H-pyran-2,3,4,5-tetrayl tetraacetate (1.0 g, 2.56 mmol, mixture of 2-α and 2-β), 4-methoxytoluene (0.65 mL, 5.12 mmol) and silver trifluoroacetate (0.85 g, 3.84 mmol) in dichloromethane (5.0 mL) at room temperature was added a solution of tin(IV) chloride (7.7 mL, 1.0 M in dichloromethane) dropwise. The reaction solution was stirred under nitrogen for 4 hours and then it was quenched with aqueous sodium bicarbonate and extracted with ethyl acetate (3×). The combined organic extract was washed with brine, dried over sodium sulfate and concentrated in vacuo. The crude product was purified by flash column chromatography (eluent: hexanes/ethyl acetate) to give (3R,4R,5R,6S)-2-(acetoxymethyl)-6-(2-methoxy-5-methylphenyl)tetrahydro-2H-pyran-3,4,5-triyl triacetate (0.88 g, 76%) as a orange oil: $^1$H NMR (CDCl$_3$, 500 MHz) δ 7.18 (d, J=2.0 Hz, 1H), 7.07-7.05 (m, 1H), 6.75 (d, J=8.5 Hz, 1H), 5.35 (t, J=9.5 Hz, 1H), 5.28 (t, J=9.0 Hz, 1H), 5.23 (t, J=9.5 Hz, 1H), 4.92 (d, J=9.5 Hz, 1H), 4.28 (dd, J=12.5, 5.0 Hz, 1H), 4.14 (dd, J=12.0, 2.5 Hz, 1H), 3.84 (ddd, J=10.0, 5.0, 2.5 Hz, 1H), 3.80 (s, 3H), 2.28 (s, 3H), 2.08 (s, 3H), 2.05 (s, 3H), 2.00 (s, 3H), 1.77 (s, 3H).

Step B: A mixture of the product from step A (0.16 g, 0.36 mmol), NBS (70.5 mg, 0.40 mmol) and AIBN (17.8 mg, 0.11 mmol) in carbon tetrachloride (5.0 mL) was heated to reflux under nitrogen. Upon completion, the reaction solution was concentrated in vacuo and the residue obtained was purified by flash column chromatography to give (3R,4R,5R,6S)-2-(acetoxymethyl)-6-(5-(bromomethyl)-2-methoxyphenyl)tetrahydro-2H-pyran-3,4,5-triyl triacetate (80.4 mg, 41%): $^1$H NMR (CDCl$_3$, 300 MHz) δ 7.39 (d, J=2.1 Hz, 1H), 7.33 (dd, J=8.4, 2.1 Hz, 1H), 6.83 (d, J=8.7 Hz, 1H), 5.36-5.25 (m, 2H), 5.23 (t, J=9.6 Hz, 1H), 4.88 (d, J=9.6 Hz, 1H), 4.50 (d, J=9.6 Hz, 1H), 4.46 (d, J=10.2 Hz, 1H), 4.28 (dd, J=12.3, 4.8 Hz, 1H), 4.17-4.11 (m, 1H), 3.86-3.80 (m, 1H), 3.85 (s, 3H), 2.09 (s, 3H), 2.06 (s, 3H), 2.01 (s, 3H), 1.77 (s, 3H).

Step C: To a solution of the product (83 mg, 0.15 mmol) from step B and 6-chloro-[1,2,4]triazolo[4,3-a]pyridin-3(2H)-one (29.3 mg, 0.17 mmol) in DMF (5.0 mL) was added cesium carbonate (0.11 g, 0.35 mmol) and then heated at 60° C. overnight. The reaction solution was cooled to room temperature, diluted with methanol (10 mL) and added potassium carbonate (43.2 mg, 0.31 mmol) to it. The resultant mixture was stirred at room temperature until complete loss of starting material. The reaction solution was then diluted with 9:1 mixture of dichloromethane/methanol, filtered through a syringe filter and concentrated in vacuo. The residue obtained was purified by preparative thin layer chromatography (dichloromethane/methanol 9:1) to give 6-chloro-2-(4-methoxy-3-((2S,3R,4R,5S,6R)-3,4,5-trihydroxy-6-(hydroxymethyl)tetrahydro-2H-pyran-2-yl)benzyl)-[1,2,4]triazolo[4,3-a]pyridin-3(2H)-one (26.7 mg, 39%): $^1$H NMR (CD$_3$OD, 500 MHz) δ 7.94 (t, J=1.5 Hz, 1H), 7.48 (d, J=2.5 Hz, 1H), 7.30 (dd, J=8.5, 2.0 Hz, 1H), 7.20-7.17 (m, 2H), 6.95 (d, J=8.5 Hz, 1H), 5.09 (s, 2H), 4.68 (d, J=9.5 Hz, 1H), 3.84 (dd, J=12.0, 2.5 Hz, 1H), 3.80 (s, 3H), 3.65 (dd, J=12.0, 7.0 Hz, 1H), 3.53-3.45 (m, 2H), 3.42-3.35 (m, 2H); ESI MS m/z 452 [M+H]$^+$.

Examples of compounds of formulae (I) and (II) prepared following similar procedures to those described in Examples 1-3 are listed in Table I below:

TABLE I

| Ex | STRUCTURE | DATA |
|---|---|---|
| I-1 | 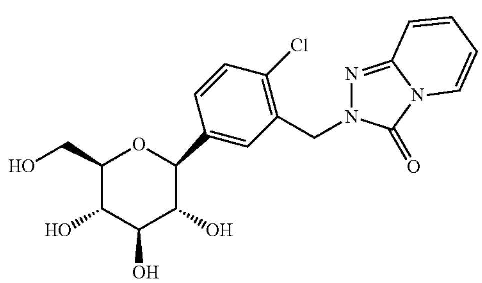 [SMILES: O=c1n(Cc2cc([C@@H]3O[C@H](CO)[C@@H](O)[C@H](O)[C@H]3O)ccc2Cl)nc2ccccn12] | $^1$H NMR (CD$_3$OD, 500 MHz) δ 7.86-7.84 (m, 1H), 7.41 (d, J = 1.0 Hz, 2H), 7.37 (s, 1H), 7.25 (ddd, J = 9.5, 6.5, 1.0 Hz, 1H), 7.15-7.12 (m, 1H), 6.68 (td, J = 7.5, 1.0 Hz, 1H), 5.28 (s, 2H), 4.10 (d, J = 9.5 Hz, 1H), 3.85 (dd, J = 12.0, 1.5 Hz, 1H), 3.67 (dd, J = 12.0, 5.5 Hz, 1H), 3.44-3.25 (m, 4H); ESI MS m/z 422 [M + H]$^+$. |
| I-2 | 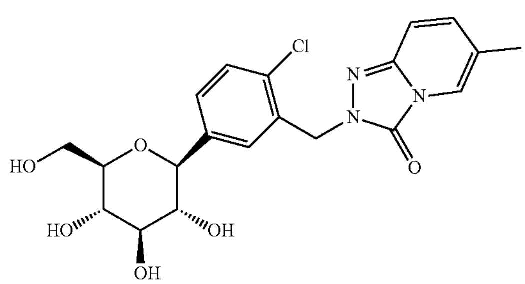 [SMILES: Cc1ccc2nn(Cc3cc([C@@H]4O[C@H](CO)[C@@H](O)[C@H](O)[C@H]4O)ccc3Cl)c(=O)n2c1] | $^1$H NMR (CD$_3$OD, 300 MHz) δ 7.63 (q, J = 1.2 Hz, 1H), 7.41-7.40 (m, 2H), 7.35 (s, 1H), 7.16 (dd, J = 9.6, 1.8 Hz, 1H), 7.08 (dd, J = 9.6, 0.6 Hz, 1H), 5.27 (s, 2H), 4.10 (d, J = 9.6 Hz, 1H), 3.85 (dd, J =12.0, 1.5 Hz, 1H), 3.67 (dd, J = 12.0, 5.7 Hz, 1H), 3.44-3.23 (m, 4H), 2.23 (d, J = 1.2 Hz, 3H); ESI MS m/z 436 [M + H]$^+$. |
| I-3 | 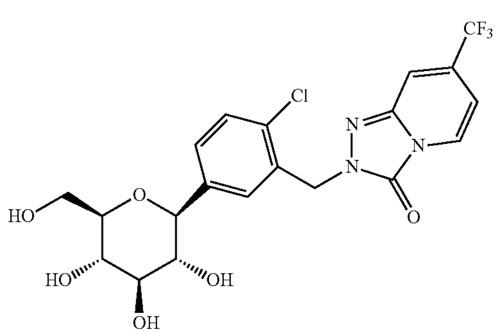 [SMILES: O=c1n(Cc2cc([C@@H]3O[C@H](CO)[C@@H](O)[C@H](O)[C@H]3O)ccc2Cl)nc2cc(C(F)(F)F)ccn12] | $^1$H NMR (CD$_3$OD, 300 MHz) δ 8.02 (d, J = 7.5 Hz, 1H), 7.59 (q, J = 1.2 Hz, 1H), 7.41-7.40 (m, 2H), 7.37 (s, 1H), 6.79 (dd, J = 7.5, 1.5 Hz, 1H), 5.32 (s, 2H), 4.10 (d, J = 9.3 Hz, 1H), 3.85 (dd, J = 12.9, 1.8 Hz, 1H), 3.80 (dd, J = 12.0, 5.1 Hz, 1H), 3.44-3.25 (m, 4H); ESI MS m/z 490 [M + H]$^+$. |

TABLE I-continued

| Ex | STRUCTURE | DATA |
| --- | --- | --- |
| I-4 | 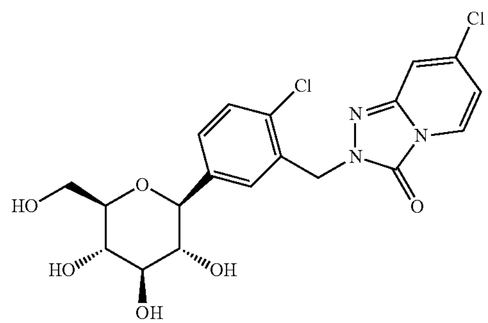 [SMILES: O=c1n(Cc2cc([C@@H]3O[C@H](CO)[C@@H](O)[C@H](O)[C@H]3O)ccc2Cl)nc2cc(Cl)ccn12] | $^1$H NMR (CD$_3$OD, 300 MHz) δ 7.86 (d, J = 7.2 Hz, 1H), 7.40 (app s, 2H), 7.36 (s, 1H), 7.25 (d, J = 0.9 Hz, 1H), 6.67 (dd, J = 7.5, 1.8 Hz, 1H), 5.25 (s, 2H), 4.10 (d, J = 9.3 Hz, 1H), 3.86 (d, J = 11.1 Hz, 1H), 3.67 (dd, J = 12.0, 4.8 Hz, 1H), 3.44-3.22 (m, 4H); ESI MS m/z 457 [M + H]$^+$. |
| I-5 | 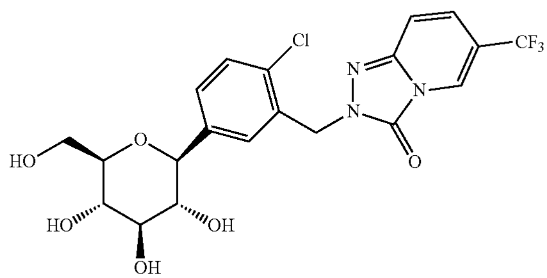 [SMILES: O=c1n(Cc2cc([C@@H]3O[C@H](CO)[C@@H](O)[C@H](O)[C@H]3O)ccc2Cl)nc2ccc(C(F)(F)F)cn12] | $^1$H NMR (CD$_3$OD, 500 MHz) δ 8.31 (q, J = 1.5 Hz, 1H), 7.41 (s, 2H), 7.38 (s, 1H), 7.35 (dd, J = 9.5, 1.5 Hz, 1H), 7.31 (d, J = 9.5 Hz, 1H), 5.29 (s, 2H), 4.10 (d, J = 9.5 Hz, 1H), 3.85 (dd, J = 12.0, 2.0 Hz, 1H), 3.68 (dd, J = 12.0, 5.5 Hz, 1H), 3.44-3.25 (m, 4H); ESI MS m/z 490 [M + H]$^+$. |
| I-6 | 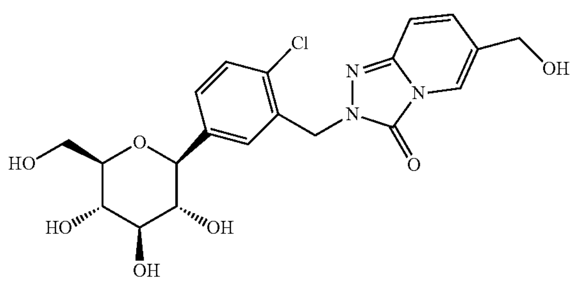 [SMILES: O=c1n(Cc2cc([C@@H]3O[C@H](CO)[C@@H](O)[C@H](O)[C@H]3O)ccc2Cl)nc2ccc(CO)cn12] | $^1$H NMR (CD$_3$OD, 500 MHz) δ 7.80 (t, 7 = 1.5 Hz, 1H), 7.41 (d, J = 1.0 Hz, 2H), 7.37 (s, 1H), 7.26 (dd, J = 9.5, 6.5 Hz, 1H), 7.14 (dd, J = 9.5, 1.0 Hz, 1H), 5.28 (s, 2H), 4.51 (d, J = 1.0 Hz, 2H), 4.10 (d, J = 9.5 Hz, 1H), 3.86 (dd, J = 12.0, 1.5 Hz, 1H), 3.67 (dd, J = 12.0, 5.5 Hz, 1H), 3.44-3.28 (m, 4H); ESI MS m/z 452 [M + H]$^+$. |
| I-7 | 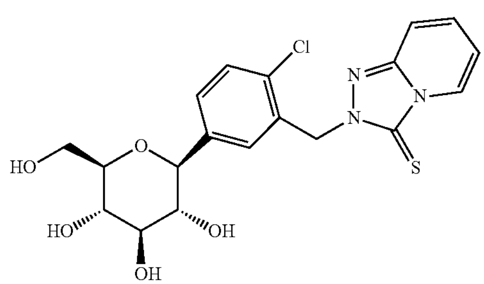 | ESI MS m/z 438 [M + H]$^+$. |
| I-8 | 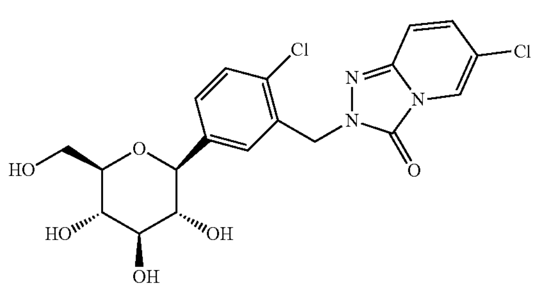 [SMILES: O=c1n(Cc2cc([C@@H]3O[C@H](CO)[C@@H](O)[C@H](O)[C@H]3O)ccc2Cl)nc2ccc(Cl)cn12] | $^1$H NMR (CD$_3$OD, 500 MHz) δ 7.97 (s, 1H), 7.41 (s, 2H), 7.36 (s, 1H), 7.22 (dd, J = 9.5, 1.5 Hz, 1H), 7.18 (dd, J = 9.5, 1.5 Hz, 1H), 5.28 (s, 2H), 4.10 (d, J = 9.5 Hz, 1H), 3.86 (dd, J = 12.0, 2.0 Hz, 1H), 3.68 (dd, J = 12.0, 2.5 Hz, 1H), 3.45-3.24 (m, 4H); ESI MS m/z 456 [M + H]$^+$. |

TABLE I-continued

| Ex | STRUCTURE | DATA |
|---|---|---|
| I-9 | 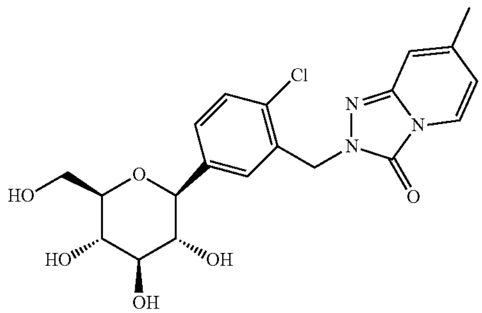 [SMILES: Cc1ccn2c(=O)n(Cc3cc([C@@H]4O[C@H](CO)[C@@H](O)[C@H](O)[C@H]4O)ccc3Cl)nc2c1] | $^1$H NMR (CD$_3$OD, 500 MHz) δ 7.75 (dd, J = 7.5, 0.5 Hz, 1H), 7.40 (s, 2H), 7.35 (s, 1H), 6.89 (d, J = 0.5 Hz, 1H), 6.55 (d, J = 7.0, 0.5 Hz, 1H), 5.24 (s, 2H), 4.10 (d, J = 9.5 Hz, 1H), 3.85 (dd, J = 12.5, 1.5 Hz, 1H), 3.67 (dd, J = 12.0, 5.0 Hz, 1H), 3.46-3.24 (m, 4H), 2.30 (s, 3H); ESI MS m/z 436 [M + H]$^+$. |
| I-10 | 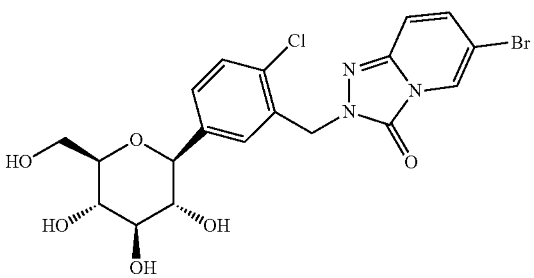 [SMILES: O=c1n(Cc2cc([C@@H]3O[C@H](CO)[C@@H](O)[C@H](O)[C@H]3O)ccc2Cl)nc2ccc(Br)cn12] | $^1$H NMR (CD$_3$OD, 500 MHz) δ 8.06 (dd, J = 2.0, 1.0 Hz, 1H), 7.41 (s, 2H), 7.36 (s, 1H), 7.30 (dd, J = 10.0, 2.0 Hz, 1H), 7.12 (dd, J = 10.0, 1.0 Hz, 1H), 5.24 (s, 2H), 4.10 (d, J = 9.5 Hz, 1H), 3.86 (dd, J = 12.0, 2.0 Hz, 1H), 3.68 (dd, J = 12.0, 5.0 Hz, 1H), 3.44-3.24 (m, 4H); ESI MS m/z 500 [M + H]$^+$. |
| I-11 | 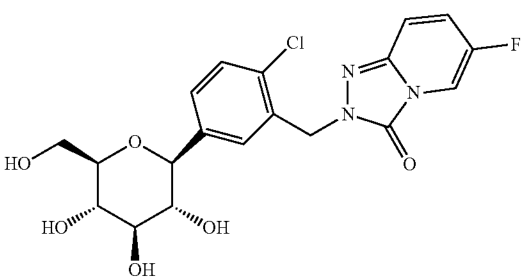 [SMILES: O=c1n(Cc2cc([C@@H]3O[C@H](CO)[C@@H](O)[C@H](O)[C@H]3O)ccc2Cl)nc2ccc(F)cn12] | $^1$H NMR (CD$_3$OD, 500 MHz) δ 7.87 (s, 1H), 7.41 (s, 2H), 7.37 (s, 1H), 7.30-7.21 (m, 2H), 5.28 (s, 2H), 4.10 (d, J = 9.5 Hz, 1H), 3.86 (dd, J = 12.0, 2.0 Hz, 1H), 3.61 (dd, J = 12.0, 2.0 Hz, 1H), 3.46-3.24 (m, 4H); ESI MS m/z 440 [M + H]$^+$. |
| I-12 | 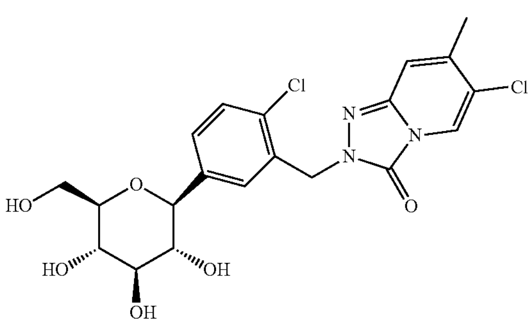 [SMILES: Cc1cc2nn(Cc3cc([C@@H]4O[C@H](CO)[C@@H](O)[C@H](O)[C@H]4O)ccc3Cl)c(=O)n2cc1Cl] | $^1$H NMR (CD$_3$OD, 500 MHz) δ 7.98 (s, 1H), 7.40 (s, 2H), 7.34 (s, 1H), 7.08 (s, 1H), 5.25 (s, 2H), 4.10 (d, J = 9.5 Hz, 1H), 3.85 (dd, J = 12.5, 2.0 Hz, 1H), 3.67 (dd, J = 12.0, 5.5 Hz, 1H), 3.45-3.24 (m, 4H), 2.35 (s, 3H); ESI MS m/z 470 [M + H]$^+$. |
| I-13 | 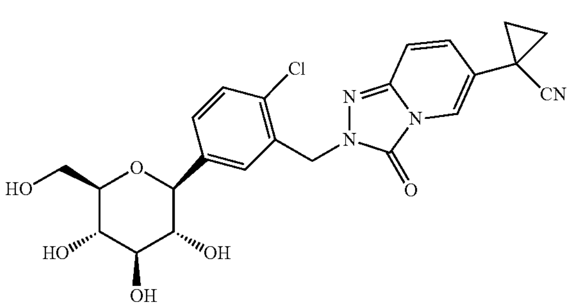 [SMILES: N#CC1(c2ccc3nn(Cc4cc([C@@H]5O[C@H](CO)[C@@H](O)[C@H](O)[C@H]5O)ccc4Cl)c(=O)n3c2)CC1] | $^1$H NMR (CD$_3$OD, 500 MHz) δ 7.90 (s, 1H), 7.40 (s, 1H), 7.34 (s, 1H), 7.35 (s, 1H), 7.24 (dd, J = 10.0, 2.0 Hz, 1H), 7.19 (dd, J = 10.0, 1.5 Hz, 1H), 5.28 (s, 2H), 4.10 (d, J = 9.5 Hz, 1H), 3.85 (dd, J = 12.5, 2.0 Hz, 1H), 3.67 (dd, J = 12.0, 5.5 Hz, 1H), 3.44-3.24 (m, 4H), 1.70 (dd, J = 8.0, 5.5 Hz, 2H), 1.51 (dd, J = 8.0, 5.5 Hz, 2H); ESI MS m/z 488 [M + H]$^+$. |

TABLE I-continued

| Ex | STRUCTURE | DATA |
|---|---|---|
| I-14 | 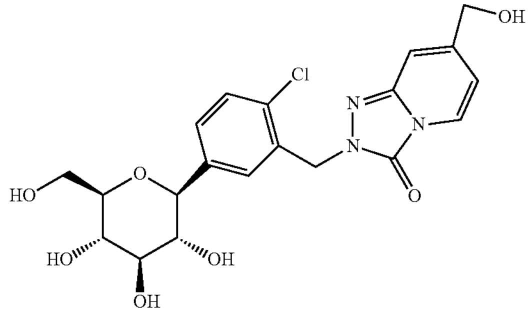 [SMILES: O=c1n(Cc2cc([C@@H]3O[C@H](CO)[C@@H](O)[C@H](O)[C@H]3O)ccc2Cl)nc2cc(CO)ccn12] | ¹H NMR (CD₃OD, 500 MHz) δ 7.81 (d, J = 7.0 Hz, 1H), 7.40 (s, 2H), 7.37 (s, 1H), 7.08 (s, 1H), 6.62 (dd, J = 7.5, 1.5 Hz, 1H), 5.26 (s, 2H), 4.54 (s, 2H), 4.10 (d, J = 9.5 Hz, 1H), 3.85 (dd, J = 12.5, 2.0 Hz, 1H), 3.67 (dd, J = 12.0, 5.5 Hz, 1H), 3.45-3.24 (m, 4H); ESI MS m/z 452 [M + H]⁺. |
| I-15 | 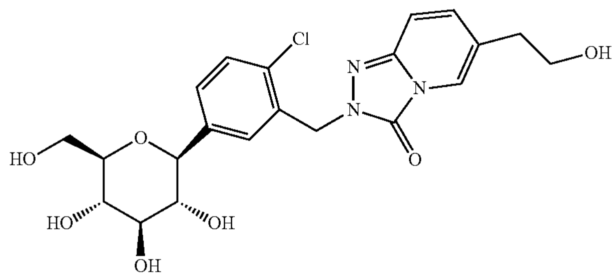 [SMILES: O=c1n(Cc2cc([C@@H]3O[C@H](CO)[C@@H](O)[C@H](O)[C@H]3O)ccc2Cl)nc2ccc(CCO)cn12] | ESI MS m/z 466 [M + H]⁺. |
| II-1 | 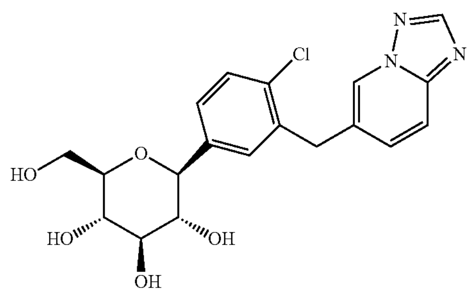 [SMILES: OC[C@H]1O[C@@H](c2ccc(Cl)c(Cc3ccc4ncnn4c3)c2)[C@H](O)[C@@H](O)[C@@H]1O] | ¹H NMR (DMS0-d6, 500 MHz) δ 8.77 (s, 1H), 8.45 (s, 1H), 7.78 (d, J = 9.5 Hz, 1H), 7.52 (dd, J = 9.0, 1.5 Hz, 1H), 7.44 (d, J = 2.0 Hz, 1H), 7.42 (d, J = 8.0 Hz, 1H), 7.29 (dd, J = 8.5, 2.0 Hz, 1H), 4.94 (t, J = 5.0 Hz, 2H), 4.84 (d, J = 5.5 Hz, 1H), 4.42 (t, J = 5.5 Hz, 1H), 4.19 (d, J = 15.0 Hz, 1H), 4.16 (d, J = 14.5 Hz, 1H), 4.01 (d, J = 9.5 Hz, 1H), 3.71-3.67 (m, 1H), 3.47-3.41 (m, 1H), 3.28-3.10 (m, 4H); ESI MS m/z 406 [M + H]⁺. |
| II-2 | 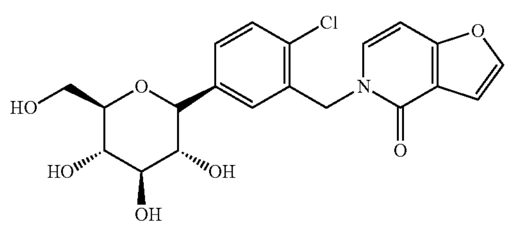 | ESI MS m/z 422 [M + H]⁺ |

Example 4

The preparation of 1-(4-(2-Chloro-5-((2S,3R,4R,5S,6R)-3,4,5-trihydroxy-6-(hydroxymethyl)tetrahydro-2H-pyran-2-yl)benzyl)phenyl)-3-ethylimidazolidine-2,4-dione Step A: To a stirred solution of (2S,3S,4R,5S)-2-(3-((tert-butyldiphenylsilyloxy)methyl)-4-chlorophenyl)-6-(hydroxymethyl)tetrahydro-2H-pyran-3,4,5-triol (1.0 g, 1.8 mmol) in dichloromethane (20 mL) at 0° C. was added dropwise N,N-diisopropylethylamine (2.4 mL, 14.7 mmol) followed by chloromethyl methyl ether (2.1 mL, 27.6 mmol). Then tetrabutylammonium iodide (2.2 g, 5.9 mmol) was added. The reaction mixture was warmed to room temperature and stirred for 24 h. The reaction was quenched with saturated sodium bicarbonate solution at 0° C. and extracted with dichloromethane (3×). The combined extracts were dried over sodium sulfate, filtered, and concentrated. The crude material obtained was purified by flash column chromatography (eluent: hexanes/ethyl acetate 100:0 to 65:35) to give compound tert-butyl(2-chloro-5-((2S,3R,4R,5R)-3,4,5-tris(methoxymethoxy)-6-((methoxymethoxy)methyl)tetrahydro-2H-pyran-2-yl)benzyloxy)diphenylsilane (1.3 g, 98%) as a colorless syrup: ¹H NMR (CDCl₃, 500 MHz) δ 7.66 (br d, J=1.3 Hz, 1H), 7.70-7.69 (m, 4H), 7.45-7.42 (m, 2H), 7.40-7.37 (m, 4H), 7.27-7.24 (m, 2H), 4.92 (d, J=6.4 Hz, 1H), 4.92 (d, J=6.2 Hz, 1H), 4.88 (d, J=6.2 Hz, 1H), 4.80 (s, 2H), 4.78 (d, J=6.4 Hz, 1H), 4.65 (d, J=6.5 Hz, 1H), 4.63 (d, J=6.4 Hz, 1H), 4.44 (d, J=6.4 Hz, 1H), 4.20 (d, J=9.4 Hz, 1H), 4.10 (d, J=6.4 Hz, 1H), 3.93 (dd, J=10.6, 1.2 Hz, 1H), 3.78 (t, J=8.8 Hz, 1H), 3.69 (dd, J=11.1, 5.3 Hz, 1H), 3.61-3.59 (m, 2H), 3.52 (t, J=9.3 Hz, 1H), 3.462 (s, 3H), 3.460 (s, 3H), 3.32 (s, 3H), 2.83 (s, 3H), 1.12 (s, 9H); ESI MS m/z 741 [M+Na]⁺.

Step B: To a stirred solution of the product from step A (1.3 g, 1.8 mmol) in tetrahydrofuran (16 mL) at 0° C. was added dropwise tetrabutylammonium fluoride (1.0 M solution in tetrahydrofuran; 2.2 mL, 2.2 mmol). The reaction mixture was warmed to room temperature and stirred for 4 h. Then it was concentrated and the crude material obtained was purified by flash column chromatography (eluent: hexanes/ethyl acetate 100:0 to 75:25) to give compound (2-chloro-5-((2S,3R,4S,5R)-3,4,5-tris(methoxymethoxy)-6-((methoxymethoxy)methyl)tetrahydro-2H-pyran-2-yl)phenyl)methanol (0.81 g, 94%) as a colorless syrup: $^{1}$H NMR (CDCl$_3$, 500 MHz) δ 7.54 (br d, J=2.0 Hz, 1H), 7.33 (d, J=8.2 Hz, 1H), 7.28 (dd, J=8.2, 2.0 Hz, 1H), 4.91 (d, J=6.4 Hz, 1H), 4.89 (d, J=6.3 Hz, 1H), 4.87 (d, J=6.3 Hz, 1H), 4.78-4.76 (m, 3H), 4.65 (s, 2H), 4.47 (d, J=6.5 Hz, 1H), 4.19 (d, J=9.5 Hz, 1H), 4.14-4.10 (m, 2H), 3.92 (dd, J=11.3, 1.6 Hz, 1H), 3.76 (t, J=8.8 Hz, 1H), 3.71 (dd, J=11.2, 5.2 Hz, 1H), 3.63-3.58 (m, 2H), 3.53 (t, J=9.4 Hz, 1H), 3.452 (s, 3H), 3.448 (s, 3H), 3.34 (s, 3H), 2.82 (s, 3H); ESI MS m/z 481 [M+H]$^{+}$.

Step C: To a stirred solution of the product from step B (470 mg, 0.98 mmol) and triethylamine (0.54 mL, 3.90 mmol) in toluene/ethyl acetate (1:1, 12 mL) at 0° C. was added dropwise methanesulfonyl chloride (0.15 mL, 1.95 mmol). The reaction mixture was stirred at 0° C. for 2 h. The white precipitate formed during the reaction was filtered off and washed with ethyl acetate. The combined filtrate and washing were concentrated. The residual oil was dissolved in acetone (6 mL) and treated with lithium bromide (850 mg, 10.0 mmol) at 0° C. After stirring at room temperature for 1 h, the reaction was quenched with water (25 mL) and extracted with ethyl acetate (4×). The combined extracts were dried over sodium sulfate, filtered, and concentrated to give compound (2S,3R,4S,5R)-2-(3-(bromomethyl)-4-chlorophenyl)-3,4,5-tris(methoxymethoxy)-6-((methoxymethoxy)methyl)tetrahydro-2H-pyran (517 mg, 97%) as a white solid: $^{1}$H NMR (CDCl$_3$, 500 MHz) δ 7.46 (d, J=2.0 Hz, 1H), 7.37 (d, J=8.3 Hz, 1H), 7.30 (dd, J=8.3, 2.0 Hz, 1H), 4.91 (d, J=6.4 Hz, 1H), 4.89-4.86 (m, 2H), 4.77 (d, J=6.4 Hz, 1H), 4.66 (s, 2H), 4.60-4.55 (m, 2H), 4.54 (d, J=6.4 Hz, 1H), 4.17 (d, J=9.4 Hz, 1H), 4.13 (d, J=6.5 Hz, 1H), 3.92 (dd, J=11.2, 1.6 Hz, 1H), 3.75 (t, J=8.8 Hz, 1H), 3.71 (dd, J=11.2, 5.2 Hz, 1H), 3.63-3.58 (m, 2H), 3.52 (t, J=9.3 Hz, 1H), 3.450 (s, 3H), 3.446 (s, 3H), 3.34 (s, 3H), 2.79 (s, 3H); ESI MS m/z 543 [M+H]$^{+}$.

Step D: A mixture of the product from step C (82 mg, 0.15 mmol), 3-ethyl-1-(4-(4,4,5,5-tetramethyl-1,3,2-dioxaborolan-2-yl)phenyl)imidazolidine-2,4-dione (which compound) (59 mg, 0.18 mmol, 1.2 equiv), sodium carbonate (48 mg, 0.45 mmol), and the palladium catalyst (0.12 mg, 0.015 mmol) in N,N-dimethylformamide/water (2:1, 2.1 mL) was heated at 80° C. under nitrogen for 4 h. The reaction was quenched with water (10 mL) and extracted with ethyl acetate (4×). The combined extracts were dried over sodium sulfate, passed through a short pad of silica gel, and concentrated. The coupling product obtained was then stirred overnight with 6 N HCl/methanol (20:1 v/v) at room temperature. The reaction mixture was concentrated to dryness and the residual material was purified by flash column chromatography (eluent: dichloromethane/methanol 100:0 to 90:10) to provide 1-(4-(2-chloro-5-((2S,3R,4R,5S,6R)-3,4,5-trihydroxy-6-(hydroxymethyl)tetrahydro-2H-pyran-2-yl)benzyl)phenyl)-3-ethylimidazolidine-2,4-dione (47 mg, 47%).

Examples of compounds of formula (III) prepared following similar procedures to those described in Example 4 are listed in Table II below:

TABLE II

| Ex | STRUCTURE | DATA |
|---|---|---|
| III-1 | 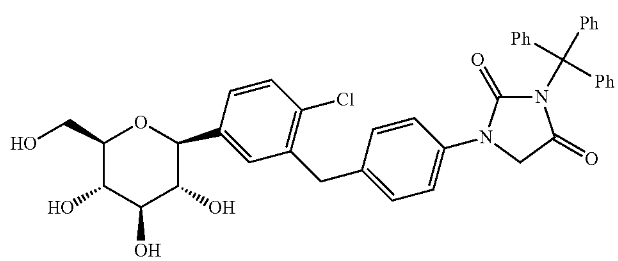 [SMILES: O=C1CN(c2ccc(Cc3cc([C@@H]4O[C@H](CO)[C@@H](O)[C@H](O)[C@H]4O)ccc3Cl)cc2)C(=O)N1C(c1ccccc1)(c1ccccc1)c1ccccc1] | 1H NMR (CD3OD, 500 MHz) δ 7.71-7.49 (m, 6H), 7.40 (br d, J = 8.7 Hz, 2H), 7.33 (d, J = 8.2 Hz, 1H), 7.32 (d, J = 1.9 Hz, 1H), 7.28 (dd, J = 8.2, 1.9 Hz, 1H), 7.25-7.22 (m, 6H), 7.18-7.16 (m, 5H), 4.35 (s, 2H), 4.12-4.02 (m, 3H), 3.86 (dd, J = 12.0, 1.8 Hz, 1H), 3.68 (dd, J = 12.0, 5.1 Hz, 1H), 3.45-3.25 (m, 4H); ESI MS m/z 727 [M + Na]$^{+}$. |
| III-2 | 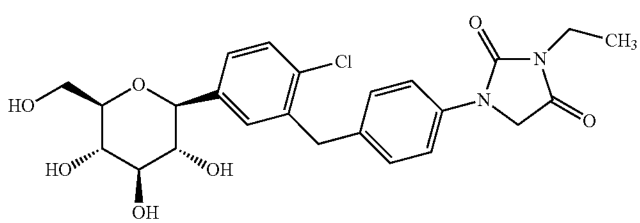 [SMILES: CCN1C(=O)CN(c2ccc(Cc3cc([C@@H]4O[C@H](CO)[C@@H](O)[C@H](O)[C@H]4O)ccc3Cl)cc2)C1=O] | $^{1}$H NMR (CD$_3$OD, 500 MHz) δ 7.52 (br d, J = 8.7 Hz, 2H), 7.36 (d, J = 2.1 Hz, 1H), 7.34 (dd, J = 8.3, 2.1 Hz, 1H), 7.29 (dd, J = 8.3, 2.1 Hz, 1H), 7.22 (br d, J = 8.7 Hz, 2H), 4.38 (s, 2H), 4.10-4.08 (m, 3H), 3.86 (dd, J = 11.9, 1.7 Hz, 1H), 3.68 (dd, J = 11.9, 5.3 Hz, 1H), 3.60 (q, J = 7.2 Hz, 2H), 3.44-3.37 (m, 3H), 3.27 (d, J = 9.0 Hz, 1H), 1.22 (t, J = 7.2 Hz, 3H); ESI MS m/z 491 [M + H]$^{+}$. |
| III-3 | 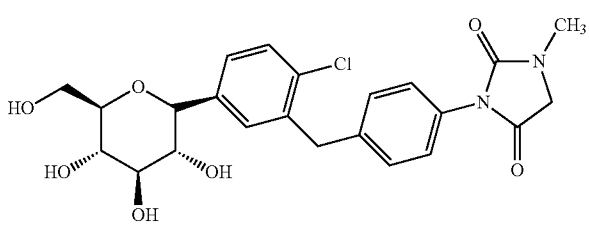 | $^{1}$H NMR (CD$_3$OD, 500 MHz) δ 7.40 (d, J = 2.0 Hz, 1H), 7.36 (d, J = 8.3 Hz, 1H), 7.33-7.29 (m, 3H), 7.26 (dt, J = 8.5, 2.0 Hz, 2H), 4.20-4.14 (m, 2H), 4.11 (d, J = 9.5 Hz, 1H), 4.08 (s, 2H), 3.87 (dd, J = 12.0, 1.8 Hz, 1H), 3.69 (dd, J = 12.0, 5.3 Hz, 1H), 3.48-3.36 (m, 3H), 3.28 (d, J = 8.9 Hz, 1H), 3.02 (s, 3H); ESI MS m/z 477 [M + H]$^{+}$. |

TABLE II-continued

| Ex | STRUCTURE | DATA |
|---|---|---|
| III-4 | [Structure: glucose-substituted phenyl with Cl, benzyl linker to N-isopropyl hydantoin] | $^1$H NMR (CD$_3$OD, 500 MHz) δ 7.50 (d, J = 8.5 Hz, 2H), 7.36-7.34 (m, 2H), 7.29 (dd, J = 8.2, 1.6 Hz, 1H), 7.22 (d, J = 8.5 Hz, 2H), 4.36 (d, J = 6.9 Hz, 1H), 4.32 (s, 2H), 4.12-4.04 (m, 3H), 3.88 (d, J = 11.7 Hz, 1H), 3.69 (dd, J = 11.9, 4.8 Hz, 1H), 3.45-3.39 (m, 3H), 3.27 (d, J = 9.1 Hz, 1H), 1.44 (d, J = 6.9 Hz, 6H); ESI MS m/z 505 [M + H]$^+$. |
| III-5 | [Structure: glucose-substituted phenyl with Cl, benzyl linker to N,5,5-trimethyl hydantoin] | $^1$H NMR (CD$_3$OD, 500 MHz) δ 7.42 (d, J = 2.0 Hz, 1H), 7.36 (d, J = 8.2 Hz, 1H), 7.33-7.30 (m, 3H), 7.21 (br d, J = 8.4 Hz, 2H), 4.17-4.10 (m, 3H), 3.86 (dd, J = 12.0, 1.6 Hz, 1H), 3.69 (dd, J = 12.0, 5.3 Hz, 1H), 3.48-3.39 (m, 3H), 3.28 (d, J = 9.0 Hz, 1H), 3.04 (s, 3H), 1.38 (s, 6H); ESI MS m/z 505 [M + H]$^+$. |

Example 5

In Vitro Assay Procedure

The inhibitory activity of the compounds of this invention against the SGLT-1 or SGLT-2 transporters can be determined by the following assay. The cDNAs for the human genes of SGLT-1 (SLC5A1—solute carrier family 5 sodium/glucose cotransporter member 1; Accession #NM_000343.1) or SGLT-2 (SLC5A2—member 2; Accession #NM_003041.2) were synthesized (OriGene Technologies, Inc.) and sub-cloned into the mammalian expression vector, pcDNA3.1 (Invitrogen Corp., Carlsbad, Calif.) using standard molecular biology techniques. CHO-K1 cells transfected with pcDNA3.1 (Invitrogen Corp., Carlsbad, Calif.) containing either the full-length hSGLT-1 or hSGLT-2 using Lipofectamine 2000 (Invitrogen Corp., Carlsbad, Calif.) were selected for stable incorporation of the construct by resistance to the selective pressure of Geneticin (450 μg/ml; Invitrogen Corp., Carlsbad, Calif.). Monoclonal cell lines isolated by minimal dilution were screened for uptake activity of radio-labled methyl α-D-glucopyranoside ([$^{14}$C]AMG), a non-metabolizable glucose analogue, and a single clone for each transporter was selected for maximal transporter activity to be used for evaluating the inhibitory activity of the compounds of this invention. In brief, 35,000 cells (CHO-K1/hSGLT-1 or CHO-K1/hSGLT-2) were plated per well of a black tissue culture treated 96-well plate in Ham's F12 media supplemented with 10% heat inactivated FBS and allowed to attached overnight at 37° C. and 5% CO$_2$. Compounds were serially diluted 3-fold in DMSO generating a nine (9) data point dose response curve for each compound. Two replicates were performed per determination. The compounds were then diluted into Uptake Buffer (10 mM Hepes, 5 mM Tris, 137 mM NaCl, 5.4 mM KCl, 2.8 mM CaCl$_2$, and 1.2 mM MgSO$_4$, pH 7.4) with a final DMSO concentration of 0.9% (v/v). After the overnight incubation and prior to compound treatment, the cells were washed twice with Sodium Free Buffer in which the sodium chloride was replaced with 137 mM Choline Chloride, and then incubated with 4 μM [$^{14}$C] AMG in Uptake Buffer in the presence or absence of diluted compound. Following a 3-hr incubation at 37° C. and 5% CO$_2$, the uptake reaction was stopped by washing the cells three (3) times with ice-cold D-PBS and then lysing the cells with 50 μl of Microscint-20. After 15-min, the amount of radioactivity that was incorporated into the cells was quantified using a Microbeta reader. Data were fit to an empirical four-parameter model to determine the inhibitor concentration at half-maximal response (IC$_{50}$). The assay window was established by control wells incubated with [$^{14}$C]AMG in the presence or absence of sodium. A dose response curve for phlorizin was generated on every plate as a positive control.

The results are shown in following Table III:

TABLE III

| Ex | SGLT2, IC50 (nM) | SGLT-1, IC50 (nM) |
|---|---|---|
| I-1 | 82.8 | 24183 |
| I-2 | 129 | 67442 |
| I-3 | 273 | 49500 |
| I-4 | 91.0 | >90000 |
| I-5 | 991 | >90000 |
| I-6 | 145 | >90000 |
| I-7 | 316 | >73192 |
| I-8 | 81.1 | 61159 |
| I-9 | 109 | >90000 |
| I-10 | 94.8 | 45634 |
| I-11 | 222 | N.A. |
| I-12 | 36.6 | >90000 |
| I-13 | 223 | >90000 |
| I-14 | 170 | >90000 |
| I-15 | 463 | >90000 |
| II-1 | 226 | >90000 |
| II-2 | 542 | 71535 |
| III-1 | 329 | 6251 |
| III-2 | 11.4 | 17483 |
| III-3 | 148 | 83 |
| III-4 | 23.6 | 35380 |
| III-5 | 489 | >90000 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:
1. A compound of formula (III):

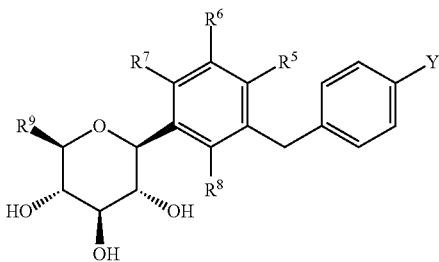

wherein
Y is

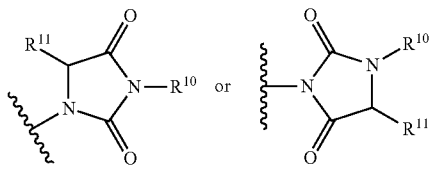

$R^5$ is Cl, F, or methyl;
$R^6$, $R^7$, and $R^8$ are H;
$R^9$ is $CH_2OH$ or SMe;
$R^{10}$ is H, lower alkyl, lower alkenyl, or lower alkynyl, wherein each lower alkyl, lower alkenyl, or lower alkynyl is optionally substituted 1-3 times by $R^e$;
$R^{11}$ is H, methyl, ethyl, or gem-dimethyl;
$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^g$-$COR^h$, or $SO_2R^g$; and
$R^g$ and $R^h$ are each, independently, H, lower alkyl, lower alkenyl, or lower alkynyl;
or an oxide thereof, a pharmaceutically acceptable salt thereof, or a solvate thereof.

2. The compound according to claim 1, wherein:
Y is

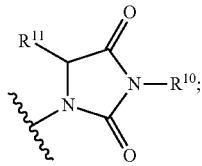

$R^5$ is Cl;
$R^6$, $R^7$, and $R^8$ are H;
$R^9$ is $CH_2OH$;
$R^{10}$ is methyl, ethyl, or isopropyl; and
$R^{11}$ is H, methyl, ethyl, or gem-dimethyl.

3. The compound according to claim 1, wherein:
Y is

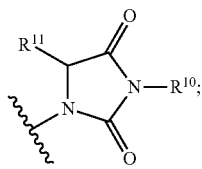

$R^5$ is Cl;
$R^6$, $R^7$, and $R^8$ are H;
$R^9$ is $CH_2OH$;
$R^{10}$ is methyl, ethyl, or isopropyl; and
$R^{11}$ is H.

4. The compound according to claim 1, wherein:
Y is

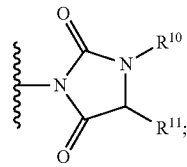

$R^5$ is Cl;
$R^6$, $R^7$, and $R^8$ are H;
$R^9$ is $CH_2OH$;
$R^{10}$ is H, H lower alkyl, lower alkenyl, or lower alkynyl, wherein each lower alkyl, lower alkenyl, or lower alkynyl is optionally substituted 1-3 times by $R^e$; and
$R^{11}$ is H, methyl, ethyl, or gem-dimethyl.

5. The compound according to claim 1, wherein the compound is selected from the group consisting of:
1-(4-(2-chloro-5-((2S,3R,4R,5S,6R)-3,4,5-trihydroxy-6-(hydroxymethyl)tetrahydro-2H-pyran-2-yl)benzyl)phenyl)-3,5,5-trimethylimidazolidine-2,4-dione;
1-(4-(2-chloro-5-((2S,3R,4R,5S,6R)-3,4,5-trihydroxy-6-(hydroxymethyl)tetrahydro-2H-pyran-2-yl)benzyl)phenyl)-3-isopropylimidazolidine-2,4-dione;
1-(4-(2-chloro-5-((2S,3R,4R,5S,6R)-3,4,5-trihydroxy-6-(hydroxymethyl)tetrahydro-2H-pyran-2-yl)benzyl)phenyl)-3-propylimidazolidine-2,4-dione;
1-(4-(2-chloro-5-((2S,3R,4R,5S,6R)-3,4,5-trihydroxy-6-(hydroxymethyl)tetrahydro-2H-pyran-2-yl)benzyl)phenyl)-3-methylimidazolidine-2,4-dione;
1-(4-(2-chloro-5-((2S,3R,4R,5S,6R)-3,4,5-trihydroxy-6-(hydroxymethyl)tetrahydro-2H-pyran-2-yl)benzyl)phenyl)imidazolidine-2,4-dione;
1-(4-(2-chloro-5-((2S,3R,4R,5S,6R)-3,4,5-trihydroxy-6-(hydroxymethyl)tetrahydro-2H-pyran-2-yl)benzyl)phenyl)-3-ethylimidazolidine-2,4-dione;
1-(4-(2-chloro-5-((2S,3R,4R,5S,6R)-3,4,5-trihydroxy-6-(hydroxymethyl)tetrahydro-2H-pyran-2-yl)benzyl)phenyl)-3-tritylimidazolidine-2,4-dione;
3-(4-(2-chloro-5-((2S,3R,4R,5S,6R)-3,4,5-trihydroxy-6-(hydroxymethyl)tetrahydro-2H-pyran-2-yl)benzyl)phenyl)-1-methylimidazolidine-2,4-dione;
3-(4-(2-chloro-5-((2S,3R,4R,5S,6R)-3,4,5-trihydroxy-6-(hydroxymethyl)tetrahydro-2H-pyran-2-yl)benzyl)phenyl)imidazolidine-2,4-dione;
3-(4-(2-chloro-5-((2S,3R,4R,5S,6R)-3,4,5-trihydroxy-6-(hydroxymethyl)tetrahydro-2H-pyran-2-yl)benzyl)phenyl)-1-ethylimidazolidine-2,4-dione;
3-(4-(2-chloro-5-((2S,3R,4R,5S,6R)-3,4,5-trihydroxy-6-(hydroxymethyl)tetrahydro-2H-pyran-2-yl)benzyl)phenyl)-1-isopropylimidazolidine-2,4-dione; and
3-(4-(2-chloro-5-((2S,3R,4R,5S,6R)-3,4,5-trihydroxy-6-(hydroxymethyl)tetrahydro-2H-pyran-2-yl)benzyl)phenyl)-1-propylimidazolidine-2,4-dione.

6. A pharmaceutical composition comprising a therapeutically effective amount of the compound according to claim 1 and a pharmaceutically acceptable carrier.

7. A compound of formula (III):

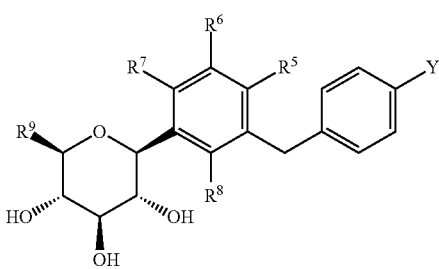

wherein
Y is

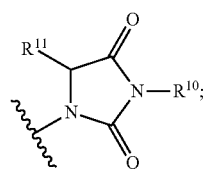

$R^5$ is Cl or methyl;
$R^6$, $R^7$, and $R^8$ are H;
$R^9$ is $CH_2OH$;
$R^{10}$ is H, H lower alkyl, lower alkenyl, or lower alkynyl, wherein each lower alkyl, lower alkenyl, or lower alkynyl is optionally substituted 1-3 times by $R^e$;
$R^{11}$ is H, methyl, ethyl or gem-dimethyl;
$R^e$ is halogen, $CF_3$, $CF_2H$, $OCF_3$, $OCF_2H$, CN, $OR^g$, $NR^gR^h$, $COR^g$, $CONR^gR^h$, $NR^gCOR^h$, $SO_2R^g$, 3 to 10-membered carbocycle, or 3 to 10-membered heterocycle, wherein the each of the 3 to 10-membered carbocycle or 3-10-membered heterocycle is optionally substituted 1-3 times with halogen, $CF_3$, $CF_2H$, $OCF_3$, $OCF_2H$, CN, $OR^g$, $NR^gR^h$, $COR^g$, $CONR^gR^h$, $NR^g$-$COR^h$, or $SO_2R^g$; and
$R^g$ and $R^h$ are each, independently, H, lower alkyl, lower alkenyl, or lower alkynyl;
or an oxide thereof, a pharmaceutically acceptable salt thereof, or a solvate thereof.

* * * * *